United States Patent
Schenberger et al.

(10) Patent No.: US 8,622,936 B2
(45) Date of Patent: *Jan. 7, 2014

(54) STRAIN MONITORING SYSTEM AND APPARATUS

(75) Inventors: Deborah Schenberger, Portland, OR (US); Somin Eunice Lee, Fair Oaks, CA (US); Amjad Ramahi, Carmichael, CA (US)

(73) Assignee: Deborah Schenberger (Munro), Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/304,666

(22) Filed: Nov. 27, 2011

(65) Prior Publication Data

US 2012/0136229 A1    May 31, 2012

Related U.S. Application Data

(63) Continuation of application No. 11/620,980, filed on Jan. 8, 2007, now Pat. No. 8,066,650, and a continuation of application No. PCT/US2005/024340, filed on Jul. 8, 2005.

(60) Provisional application No. 60/586,593, filed on Jul. 8, 2004.

(51) Int. Cl.
*A61B 5/103* (2006.01)
*A61B 5/117* (2006.01)
*G01L 1/00* (2006.01)

(52) U.S. Cl.
USPC ........... 600/587; 600/593; 600/594; 600/595; 73/862.626; 73/862.68

(58) Field of Classification Search
USPC ........ 600/587, 593–595; 73/862.626, 862.68, 73/862.69
See application file for complete search history.

(56) References Cited

U.S. PATENT DOCUMENTS 4,941,363 A * 7/1990 Doemens et al. ........ 73/862.337
5,025,346 A    6/1991 Tang et al.
(Continued)

FOREIGN PATENT DOCUMENTS

EP    1 113 252 A1    7/2001
WO    9926530 A1    6/1999
(Continued)

OTHER PUBLICATIONS

Castelli, F.—"The Thin Dielectric Film Capacitive Displacement Transducer to Nanometer"—IEEE Trans. on Intstrumentation and Measurement, vol. 50, No. 1, Feb. 2001, pp. 106-110.

(Continued)

*Primary Examiner* — Rene Towa
*Assistant Examiner* — Adam Eiseman
(74) *Attorney, Agent, or Firm* — John P. O'Banion

(57) ABSTRACT

A system for monitoring strain as an indicator of biological conditions, such as spinal fusion, glucose levels, spinal loading, and heart rate. The system includes an inter-digitated capacitor sensor, and RF transmitter, and an associated antenna, all of which are microminiature or microscopic in size and can be implanted in a biological host such as a human or animal. An inductively coupled power supply is also employed to avoid the need for implantation of chemical batteries. Power is provided to the sensor and transmitter, and data is transmitted from the sensor, when an external receiving device, such as a handheld RF ID type receiver, is placed proximate the location of the implanted sensor, transmitter and inductively coupled power supply. The implanted sensor, transmitter and inductively coupled power supply can be left in place permanently or removed when desired.

19 Claims, 29 Drawing Sheets

(56) References Cited

U.S. PATENT DOCUMENTS

| | | | |
|---|---|---|---|
| 5,610,528 A * | 3/1997 | Neely et al. | 324/660 |
| 5,750,904 A * | 5/1998 | Doemens et al. | 73/862.623 |
| 5,807,258 A | 9/1998 | Cimochowski et al. | |
| 5,827,980 A * | 10/1998 | Doemens et al. | 73/862.626 |
| 5,935,086 A | 8/1999 | Beacon et al. | |
| 6,092,530 A | 7/2000 | Weissman et al. | |
| 6,170,488 B1 | 1/2001 | Spillman et al. | |
| 6,206,835 B1 | 3/2001 | Spillman et al. | |
| 6,223,138 B1 | 4/2001 | Raffius et al. | |
| 6,432,050 B1 | 8/2002 | Porat et al. | |
| 6,433,629 B2 | 8/2002 | Hamel et al. | |
| 6,532,824 B1 * | 3/2003 | Ueno et al. | 73/780 |
| 6,810,750 B1 | 11/2004 | Kiefer et al. | |
| 7,017,404 B1 | 3/2006 | Kain | |
| 7,085,122 B2 | 8/2006 | Wu et al. | |
| 7,509,870 B2 | 3/2009 | Aebersold et al. | |
| 8,066,650 B2 | 11/2011 | Lee et al. | |
| 8,070,695 B2 | 12/2011 | Gupta et al. | |
| 2002/0050174 A1 | 5/2002 | Valdevit et al. | |
| 2002/0092340 A1 | 7/2002 | Prater et al. | |
| 2004/0011137 A1 | 1/2004 | Hnat et al. | |
| 2004/0183177 A1 | 9/2004 | Curtis et al. | |
| 2006/0032314 A1 | 2/2006 | Hnat et al. | |
| 2006/0070451 A1 | 4/2006 | Walsh et al. | |
| 2006/0075820 A1 | 4/2006 | Cobianu et al. | |
| 2007/0276294 A1 | 11/2007 | Gupta et al. | |

FOREIGN PATENT DOCUMENTS

| | | |
|---|---|---|
| WO | 0013585 A1 | 3/2000 |
| WO | 0019888 A1 | 4/2000 |
| WO | 0030534 A1 | 6/2000 |
| WO | 0215769 A2 | 2/2002 |
| WO | 02076289 A2 | 10/2002 |
| WO | 2004005872 A2 | 1/2004 |
| WO | 2004031709 A2 | 4/2004 |

OTHER PUBLICATIONS

European Patent Office, related patent application No. 05 770 030.4, Office Action issued on Jun. 13, 2012 (pp. 1-6), with claims examined (pp. 7-10), pp. 1-10.

ISA/US, International Search Report and Written Opinion (pp. 1-8) with claims (pp. 9-27) from related PCT Application No. PCT/US05/024340, issued on Dec. 4, 2006, pp. 1-27.

European Patent Office, Extended European Search Report (pp. 1-7) with claims (pp. 8-12) from related European Patent Application No. 05770030, issued on Jul. 10, 2009, counterpart to PCT Application No. PCT/US05/024340, claiming priority to U.S. Appl. No. 60/586,583, pp. 1-12.

Japanese Patent Office, English translation of Japanese Office Action (pp. 1-3) with claims (pp. 4-22) from related Japanese Patent Application No. 2007-520554, issued on Nov. 30, 2010, counterpart to PCT Application No. PCT/US05/024340, claiming priority to U.S. Appl. No. 60/586,583, pp. 1-22.

* cited by examiner

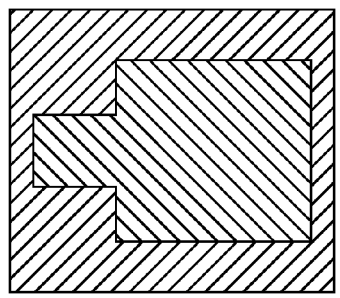
FIG. 7M
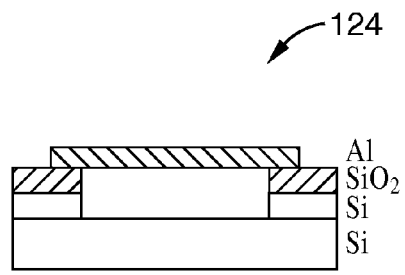
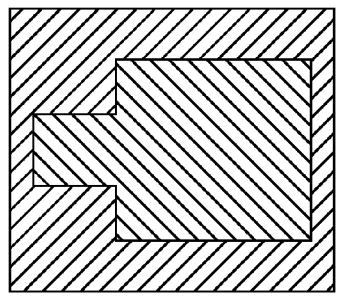
FIG. 7N
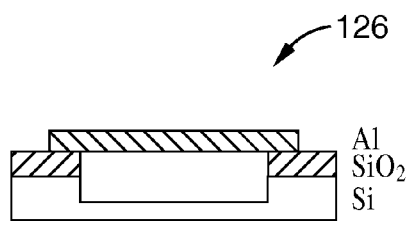
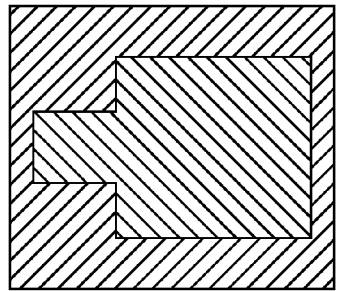
FIG. 7O
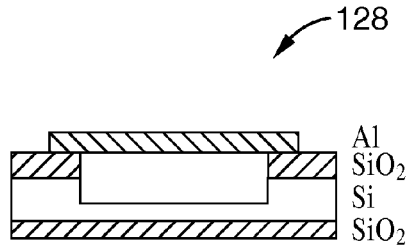
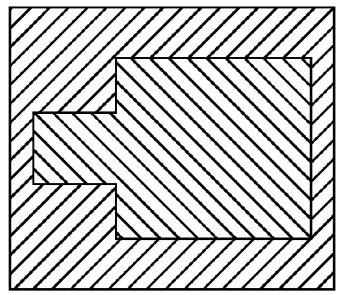
FIG. 7P
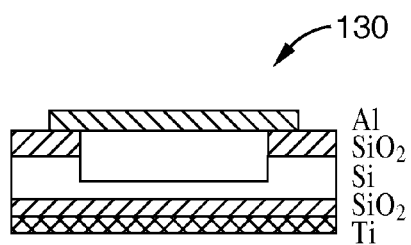

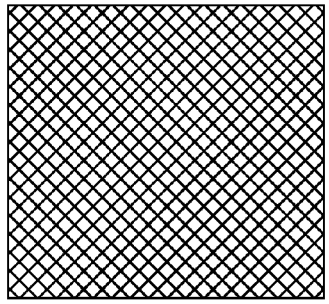
FIG. 12CC
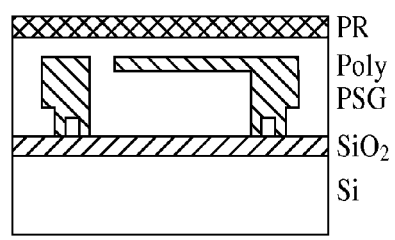
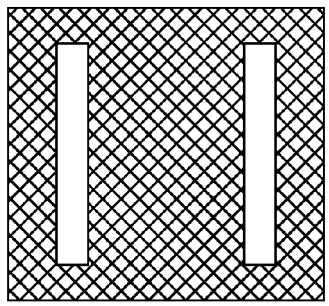
FIG. 12DD
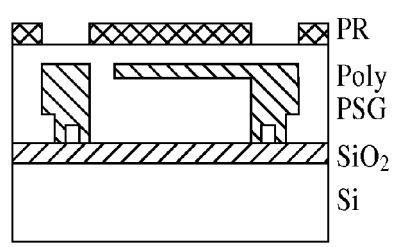
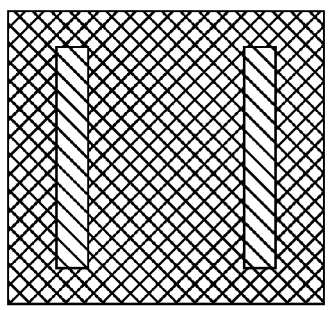
FIG. 12EE
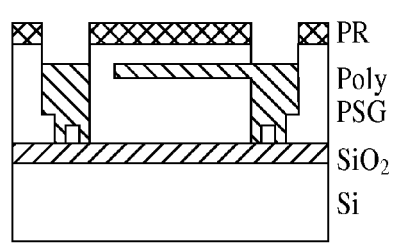
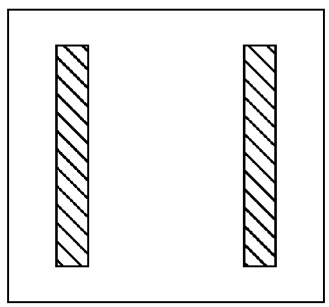
FIG. 12FF
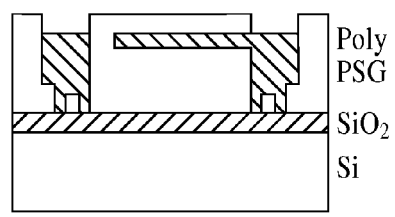

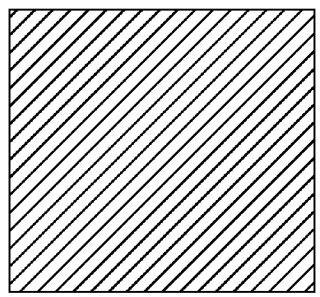
FIG. 12GG
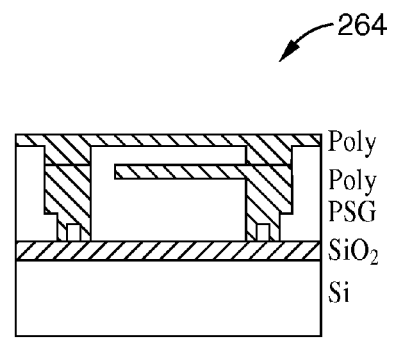
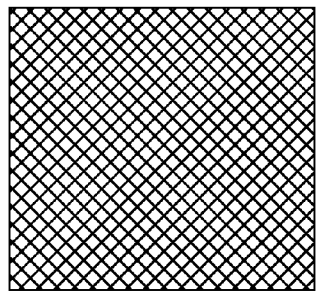
FIG. 12HH
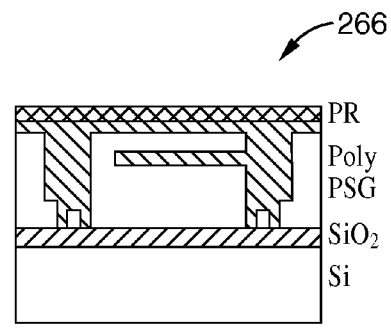
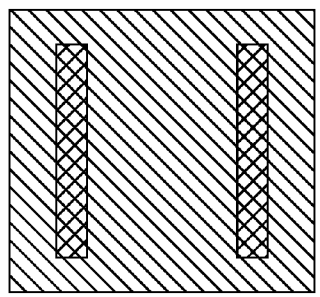
FIG. 12II
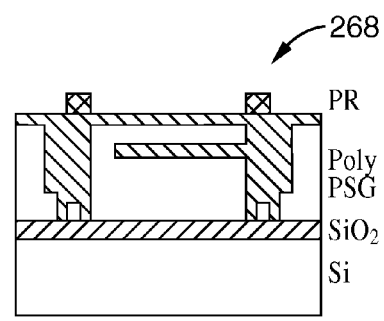
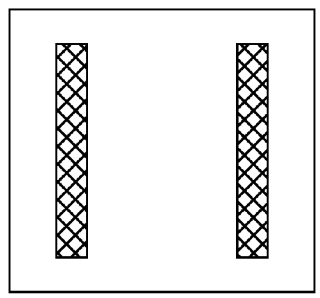
FIG. 12JJ
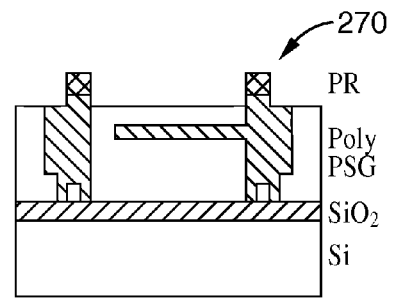

STRAIN MONITORING SYSTEM AND APPARATUS

CROSS-REFERENCE TO RELATED APPLICATIONS

This application is a continuation of U.S. patent application Ser. No. 11/620,980 filed on Jan. 8, 2007, now U.S. Pat. No. 8,066,650 issued on Nov. 29, 2011 and incorporated herein by reference in its entirety, which is a 35 U.S.C. §111 (a) continuation of PCT international application serial number PCT/US2005/024340, filed on Jul. 8, 2005 and incorporated herein by reference in its entirety, which is a nonprovisional of U.S. provisional patent application Ser. No. 60/586,593 filed on Jul. 8, 2004 and incorporated herein by reference in its entirety. Priority is claimed to each of the foregoing applications.

This application is related to PCT International Publication No. WO 2006/010037 A2, published on Jan. 29, 2006, incorporated herein by reference in its entirety.

This application is also related to U.S. patent application Ser. No. 11/620,973 filed on Jan. 8, 2007, now U.S. Pat. No. 8,070,695 issued on Dec. 6, 2011 and incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

A portion of the material in this patent document is also subject to protection under the maskwork registration laws of the United States and of other countries. The owner of the maskwork rights has no objection to the facsimile reproduction by anyone of the patent document or the patent disclosure, as it appears in the United States Patent and Trademark Office publicly available file or records, but otherwise reserves all maskwork rights whatsoever. The maskwork owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to monitoring strain, and more particularly to using strain monitoring as an indicator of medical conditions including monitoring the progress of spinal fusion, monitoring glucose levels, measuring spinal loading, and monitoring heart rate.

2. Description of Related Art

Lumbar fusion is one of the fastest growing areas of orthopedic surgery. The most common indication for surgical intervention is pain in the lower back. Although many devices have been designed to minimize the incidence of work-related back injury, as a society we still participate in many activities that lead to back injury. Most frequently, inappropriate lifting of objects, pulling or lifting objects from awkward angles, and fatigue lead to injury of the back muscles. If the level of injury is severe enough, the muscles and ligaments of the lumbar spine cannot withstand the load applied, and the intervertebral disc will become herniated from the anterior side of the spine. This is often called a herniated or ruptured disc. In addition, the vertebrae of the spine articulate with each other through the transverse and spinous processes located on the posterior aspect of the vertebrae. In between the processes, there are small pads of cartilage that can become damaged with a back injury. Both herniated discs and the processes can cause chronic pain and loss of function in the spine. Pain results in debilitation and prevents the patient from enjoying ordinary daily activities.

To eliminate the pain, a lumbar fusion is performed wherein an incision is made over the lumbar region of the spine and metal bracing is applied bilaterally to the posterior of the vertebrae. This bracing provides initial mechanical stiffness until bone growth, stimulated by a bone growth factor, encapsulates the metal bracing and eliminates motion between the two lumbar vertebrae. There are many choices for the metal bracing, called spinal instrumentation, which can be used to create the initial fixation. In general, a pedicle screw is screwed from the posterior through the pedicle bony bridge of the vertebrae and into the wall the vertebral body. This procedure is repeated for the neighboring vertebrae and bilaterally on the opposite side of the posterior spine. Once all four pedicle screws are in place, a rod or plate is placed over posts on two of the pedicle screws. The rod or plate is then held down with locking nuts that screw onto the posts. A slurry of bone and bone growth factor is applied over the spinal instrumentation and vertebrae, and the incision is closed.

After lumbar fusion surgery, rehabilitation takes several months. The patient is immobilized with a brace that extends from beneath the arms to midline of the hips and is instructed not to perform any strenuous physical activity. No lifting, driving, running or bending at the waist is allowed. Any kind of activity that involves impact is also prohibited, such as roller coasters. The patient must wear the brace until fusion is visible on an x-ray radiograph. Depending on the age of the patient, this can be anywhere from four months to a year after surgery. Because of this extended period of immobility, the muscles of the spine and abdomen atrophy from disuse. The brace also contributes to stress shielding, meaning the brace is carrying some of the spinal load, resulting in an inferior strength lumbar fusion.

The problem with the foregoing treatment approach, is that fusion occurs much sooner than is predicted by radiographs. For example, a solid fusion could occur as early as eight weeks (two months) after surgery. However, the bone that initially grows around the spinal instrumentation is trabecular bone, and although it is strong and dense, it is not radiographically opaque. Thus, it cannot be seen on an x-ray until it has been infused with minerals, such as calcium.

There are several methods for measuring the movement or strain in the human spine, including those that involve collecting an electronic signal and transmitting it to an external receiver. For example, U.S. Pat. No. 6,433,629 teaches using a Wheatstone bridge and a timing circuit to measure the displacement (strain) in an orthopedic implant. In addition, the device does not use an internal power source. Instead, a magnetic coil brought in close proximity to the Wheatstone bridge provides power to the circuitry and activates the circuitry for the duration of the measurement.

In U.S. Pat. No. 5,935,086, the relative angles between two or more joint are measured and a force transducer is used to simultaneously measure the applied force in the joint of an artificial knee. This is similar to U.S. Pat. No. 5,995,879, which also measures the angle between two freely movable points to determine the orientation of a second spinal vertebrae relative to a first vertebrae.

U.S. Pat. No. 6,432,050 uses audible acoustic feedback to monitor an in vivo sensor or device. By applying an acoustic query to the implanted device, the operator can audibly determine if the device is functioning properly. This has wide reaching applications, from heart surgery stents, to intervertebral disc implants.

In U.S. Pat. No. 6,223,138, a Wheatstone bridge is used to measure strain displacement, but the signal is amplified and added it to a carrier frequency. By adding the signal to a secondary frequency, loss of a small signal in the background noise is avoided.

Published U.S. patent application number US2002/0050174 A1 also uses strain gages in a Wheatstone bridge, the device has been adapted to successfully measure strains on the micron scale.

Published U.S. patent application number US2004/0011137 A1 also provides information concerning the current state of the art.

Each of the foregoing U.S. patents and published patent applications is incorporated herein by reference in its entirety.

Notwithstanding the foregoing approaches to measuring strain, the onset of spinal fusion after lumbar surgery continues to be difficult to determine, and patients are frequently fitted with a spinal brace for three to six months after surgery even though the implant provides internal fixation in a much shorter period of time. If a new method could be developed that could detect a solid fusion without the need for radiographic verification, the amount of time patients would need to be in a brace could be cut by 50% or more.

Similarly, there is a need for new approaches to monitoring strain in other parts of the body and for monitoring other medical conductions. The present invention satisfies those needs and advances the state of the art.

BRIEF SUMMARY OF THE INVENTION

The present invention comprises a system and apparatus that satisfies the foregoing needs through the use of four main features: strain sensing, integrated microfabricated circuitry, RF signal transmission, and data collection. According to an aspect of the invention, the sensor comprises an inter-digitated capacitor. Another aspect of the invention is the microminiaturization of a strain sensing system. Using the techniques of the present invention, a strain sensing system can be microscopic in size. The resultant miniaturization allows the system to be incorporated or integrated into an implant or other device. Another aspect of the invention is the elimination of the need for an internal battery power supply or external leads connecting the system to an external power supply. This is accomplished through the use of an inductively coupled power supply.

According to another aspect of the invention, strain monitoring is used as an indicator of medical conditions including monitoring the progress of spinal fusion, monitoring glucose levels, measuring spinal loading, and monitoring heart rate.

By way of example, and not of limitation, for monitoring spinal fusion, the inventive strain sensor system can be bonded to the implant, which will be load sharing with the bone. Thus, as the spine heals, the implant strain will diminish. In this embodiment, the invention comprises an implantable strain transduction system for humans for determining when fusion has occurred.

Accordingly, the present invention generally comprises an implantable inter-digitated capacitor based strain sensor system that can produce a reliable, reproducible signal that will indicate via a radio telemetry signal when strain has changed.

In one exemplary embodiment, the invention contains a strain sensor that will accurately measure low levels of strain and transmit the data using an RF transmitter and associated antennal. In another embodiment, the implantable portion of the system is inductively powered by an external electromagnetic power source to avoid the complications of implanting batteries within humans. Otherwise, batteries can be mounted subcutaneously and later removed.

In another embodiment, an apparatus for sensing strain comprises an inter-digitated capacitor sensor, a transmitter, and an antenna, wherein the sensor, transmitter, and antenna are adapted for implantation in a biological host.

In another embodiment, a system for sensing strain comprises an inter-digitated capacitor sensor, a transmitter, an antenna, and a receiver, wherein the sensor, transmitter, and antenna are adapted for implantation in a biological host, and wherein the receiver is a non-implantable remotely operated device.

In a further embodiment, a system for sensing strain comprises an inter-digitated capacitor sensor, a transmitter, an antenna, an inductively coupled power supply, and a receiver, wherein the sensor, transmitter, antenna, and power supply are adapted for implantation in a biological host, and wherein the receiver is a non-implantable remotely operated device.

In still another embodiment, an apparatus for sensing strain comprises an inter-digitated capacitor sensor, a transmitter, and an antenna, wherein the sensor, transmitter, and antenna are adapted for implantation in a biological host, wherein the sensor is adapted for mounting to a spinal plate and configured to produce a signal representative of strain in said spinal plate, and wherein the transmitter is configured for transmitting signals representative of strain.

Another embodiment of the invention is a system for sensing strain comprising an inter-digitated capacitor sensor, a transmitter, an antenna, and a receiver, wherein the sensor, transmitter, and antenna are adapted for implantation in a biological host, wherein the sensor is adapted for mounting to a spinal plate and configured to produce a signal representative of strain in said spinal plate, wherein the transmitter is configured for transmitting signals representative of strain, and wherein the receiver is a non-implantable remotely operated device.

A further embodiment of the invention is a system for sensing strain comprising an inter-digitated capacitor sensor, a transmitter, an antenna, an inductively coupled power supply, and a receiver, wherein the sensor, transmitter, antenna, and power supply are adapted for implantation in a biological host, wherein the sensor is adapted for mounting to a spinal plate and configured to produce signals representative of strain in the spinal plate, wherein the transmitter is configured for transmitting signals representative of strain, and wherein the receiver comprises a non-implantable remotely operated device.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

Figure 12A:
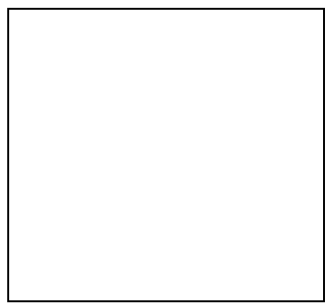
Figure 12B:
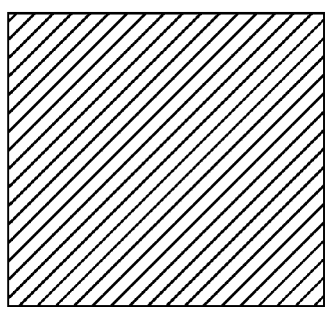
Figure 12C:
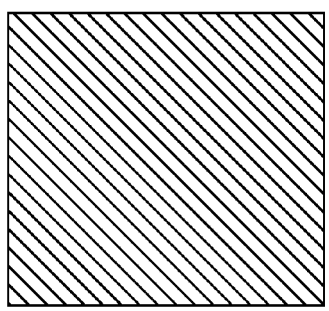
Figure 12D:
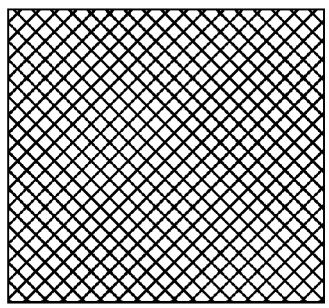
Figure 12E:
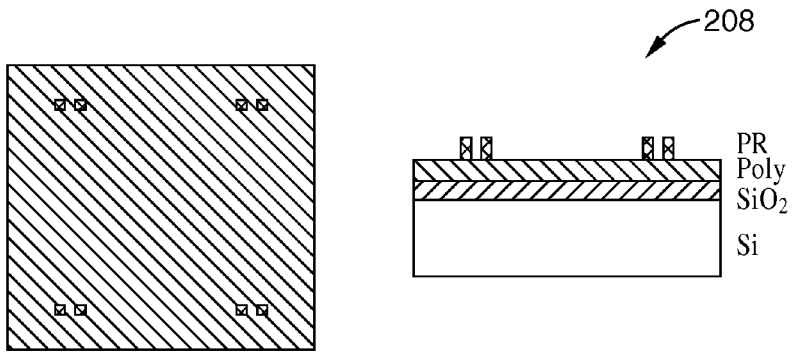
Figure 12F:
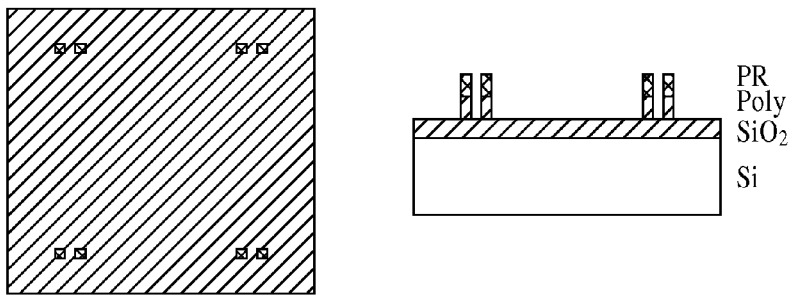
Figure 12G:
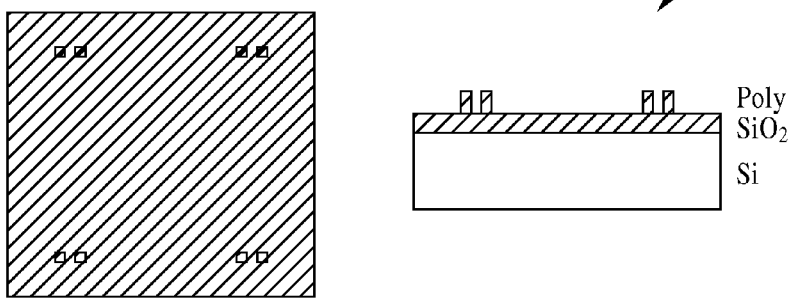
Figure 12H:
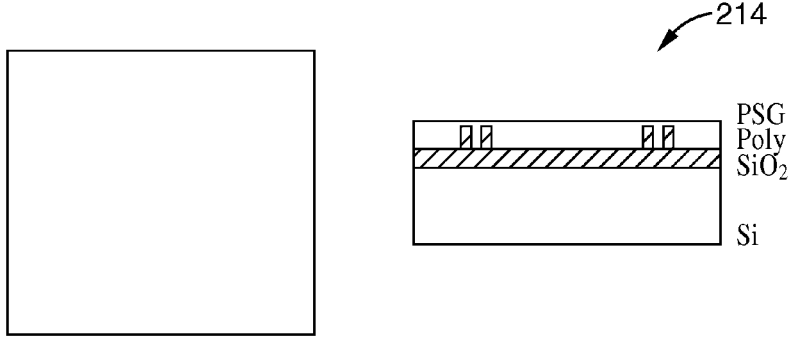
Figure 12I:
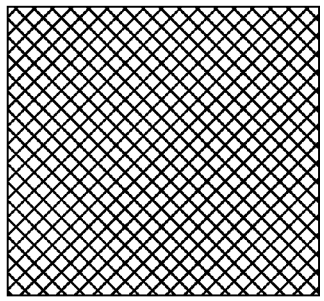
Figure 12I:
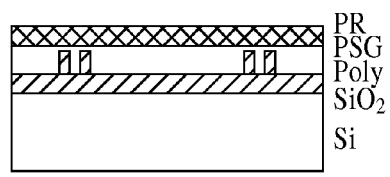
Figure 12J:
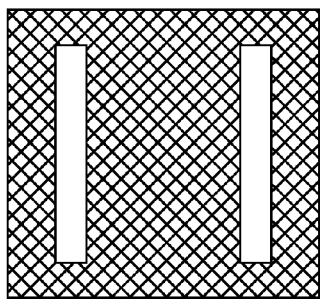
Figure 12J:
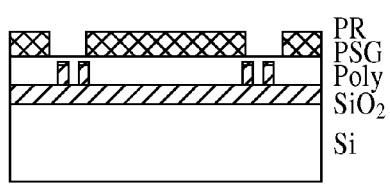
Figure 12K:
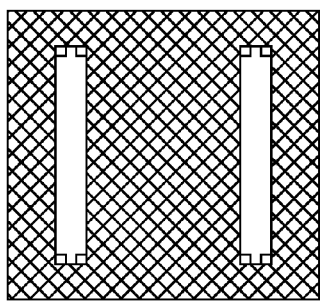
Figure 12K:
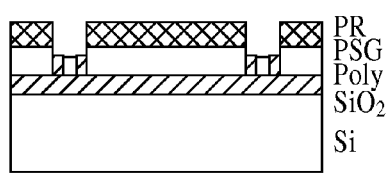
Figure 12L:
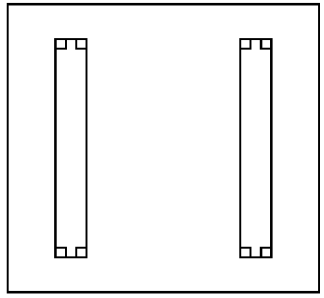
Figure 12L:
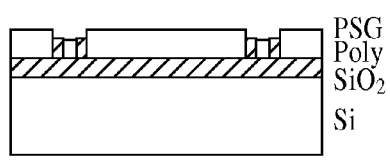
Figure 12M:
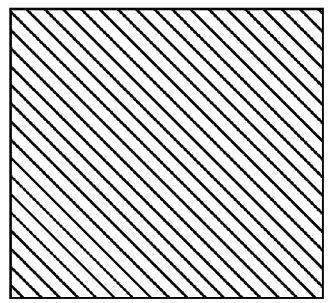
Figure 12M:
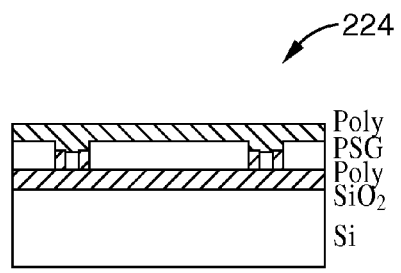
Figure 12N:
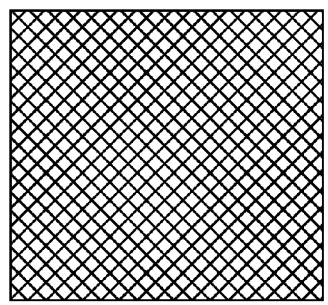
Figure 12N:
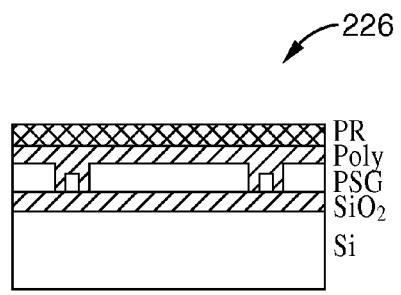
Figure 12O:
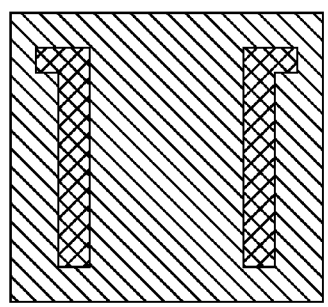
Figure 12O:
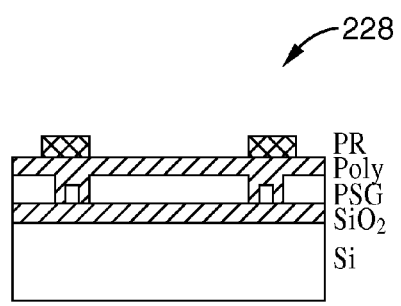
Figure 12P:
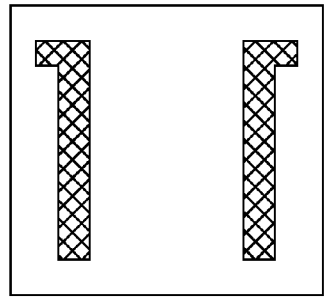
Figure 12P:
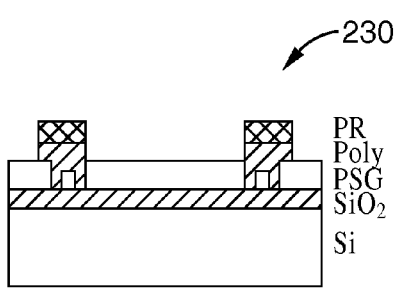
Figure 12Q:
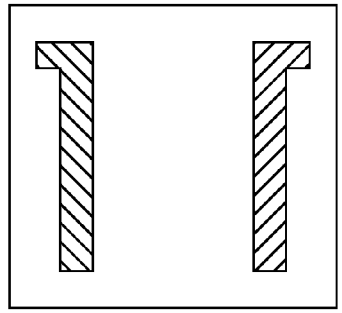
Figure 12Q:
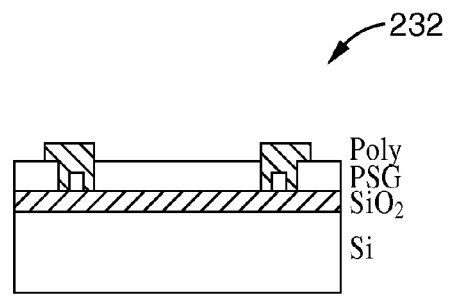
Figure 12R:
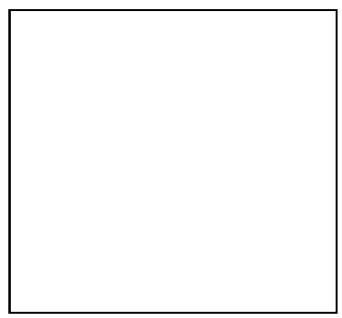
Figure 12R:
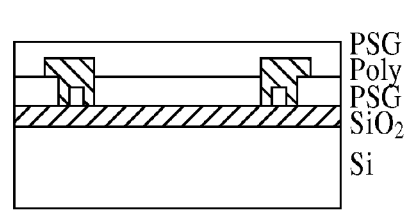
Figure 12S:
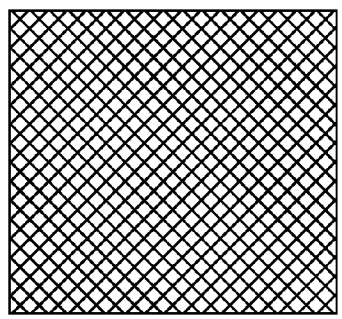
Figure 12S:
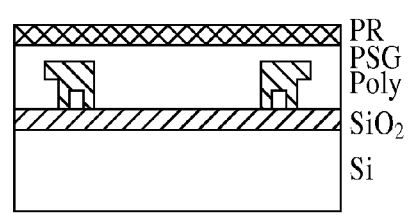
Figure 12T:
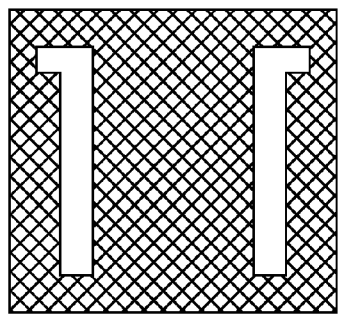
Figure 12T:
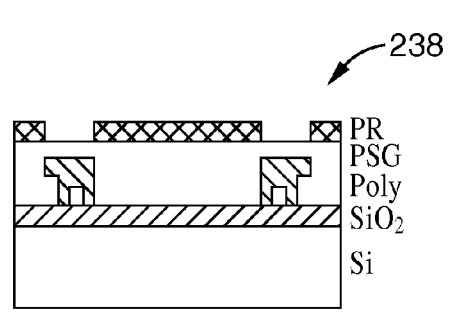
Figure 12U:
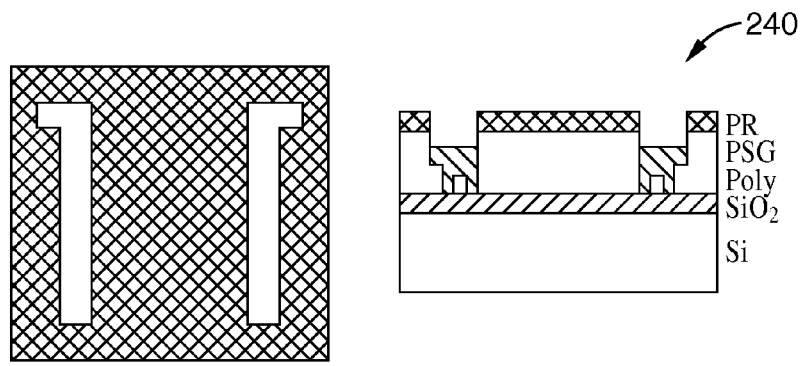
Figure 12V:
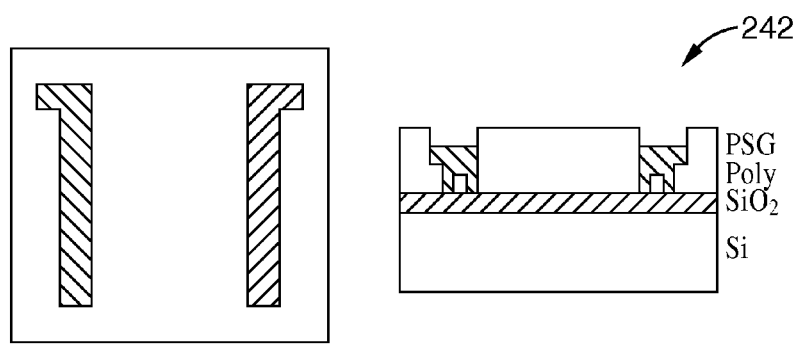
Figure 12W:
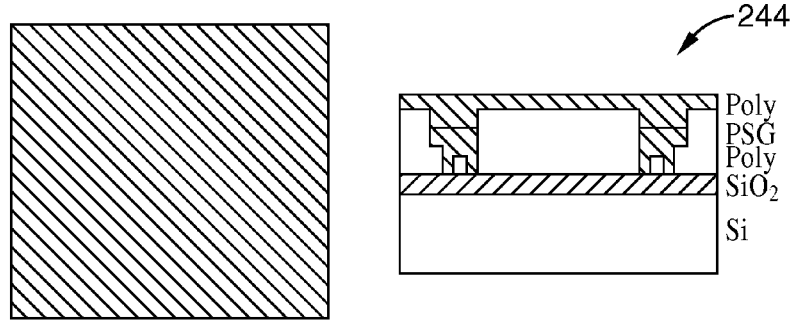
Figure 12X:
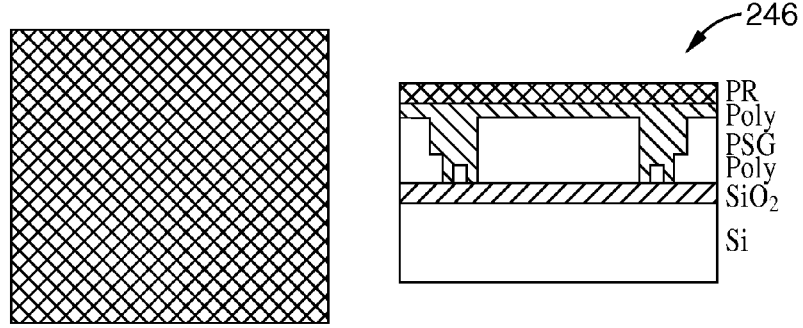
Figure 12Y:
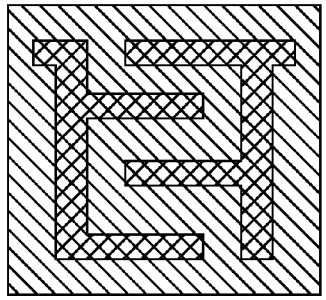
Figure 12Y:
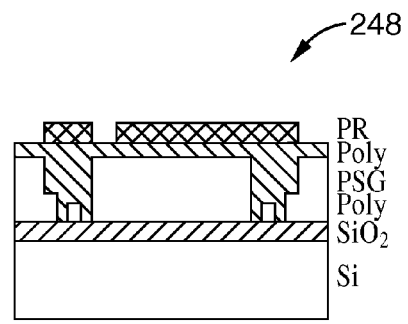
Figure 12Z:
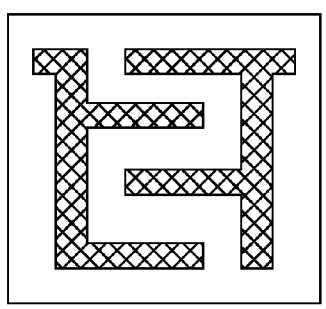
Figure 12Z:
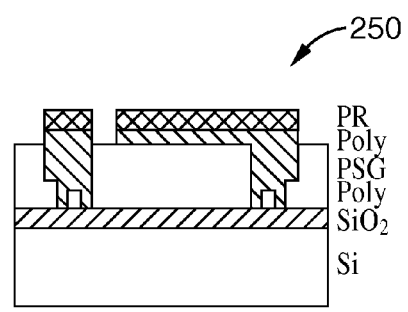
Figure 12A:
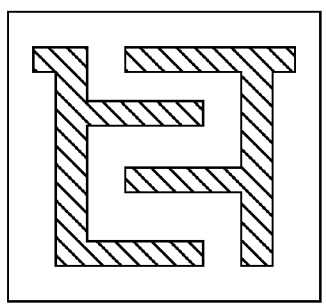
Figure 12A:
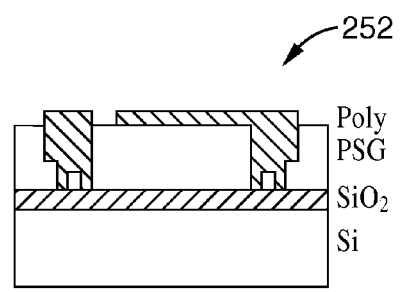
Figure 12B:
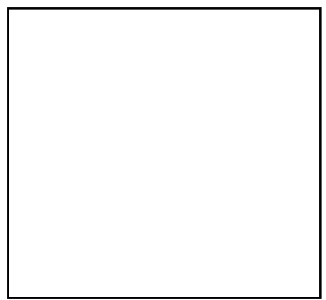
Figure 12B:
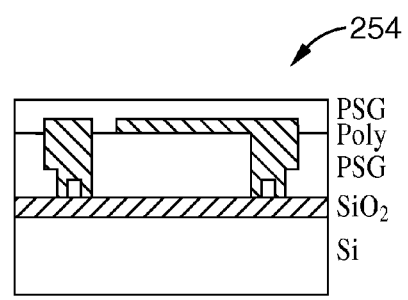
Figure 12K:
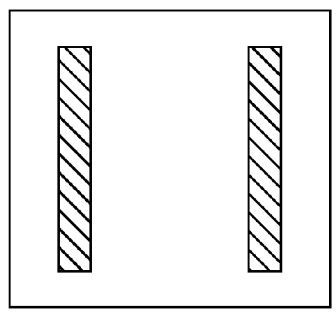
Figure 12K:
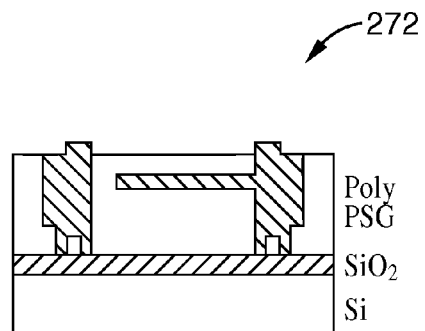
Figure 12L:
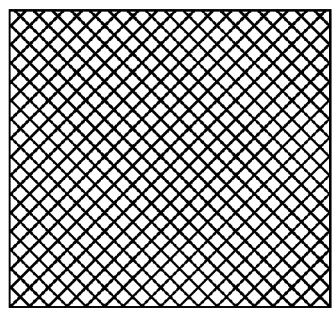
Figure 12L:
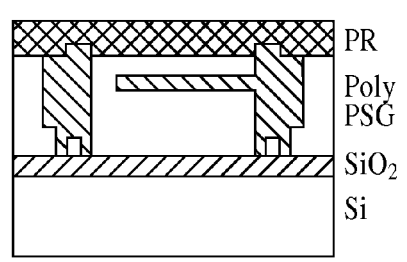
Figure 12M:
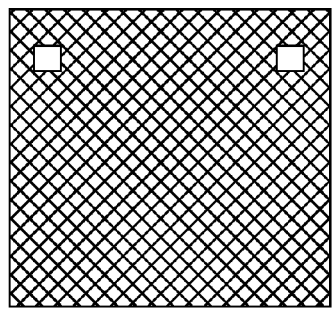
Figure 12M:
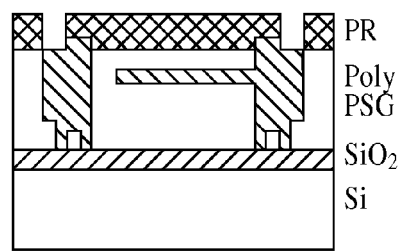
Figure 12N:
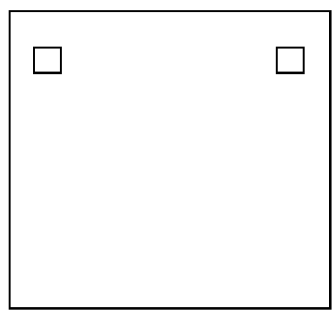
Figure 12N:
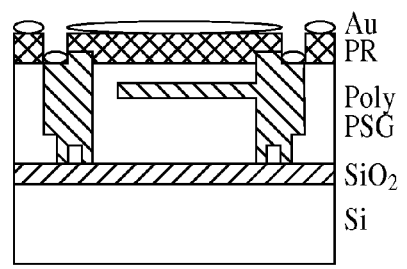
Figure 12O:
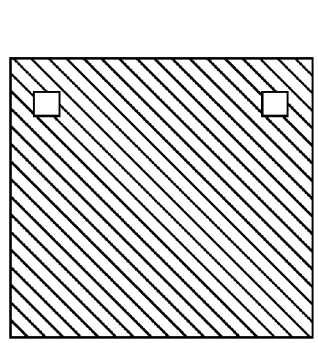
Figure 12O:
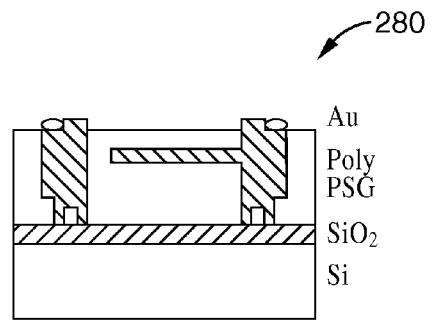
Figure 12P:
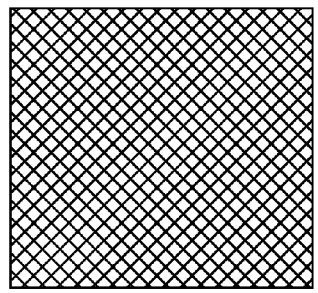
Figure 12P:
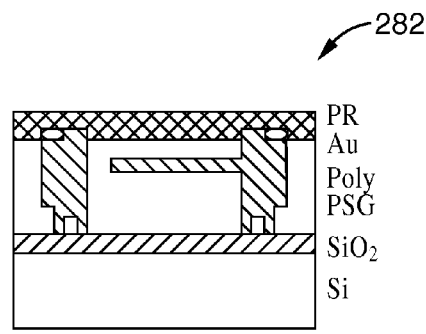
Figure 12Q:
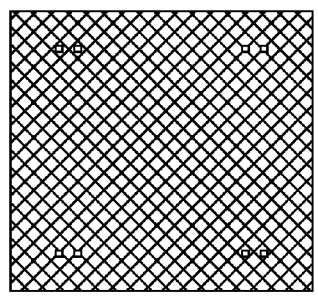
Figure 12Q:
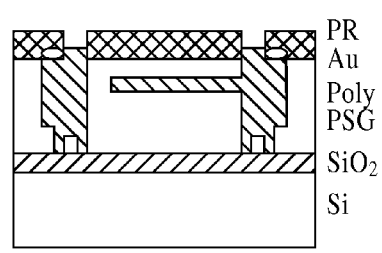
Figure 12R:
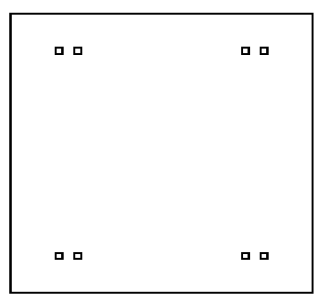
Figure 12R:
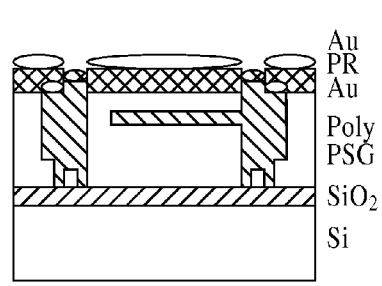
Figure 12S:
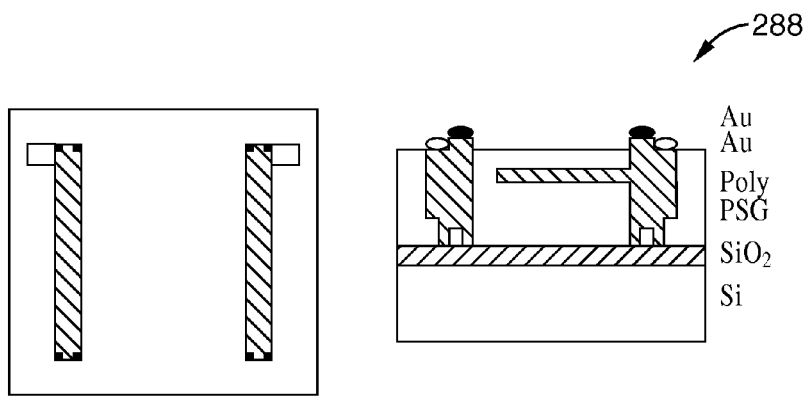
Figure 12T:
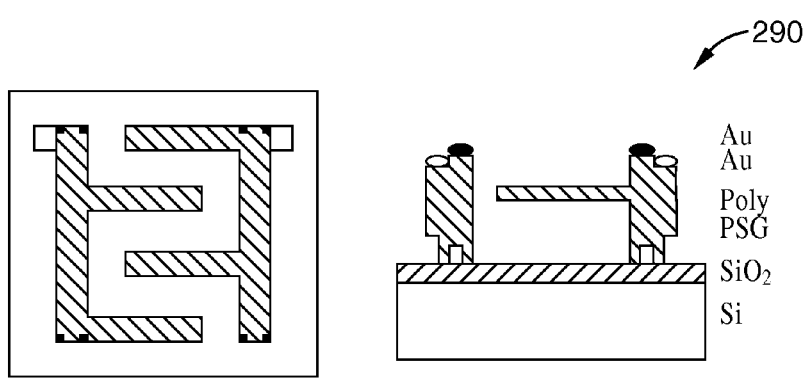
Figure 12U:
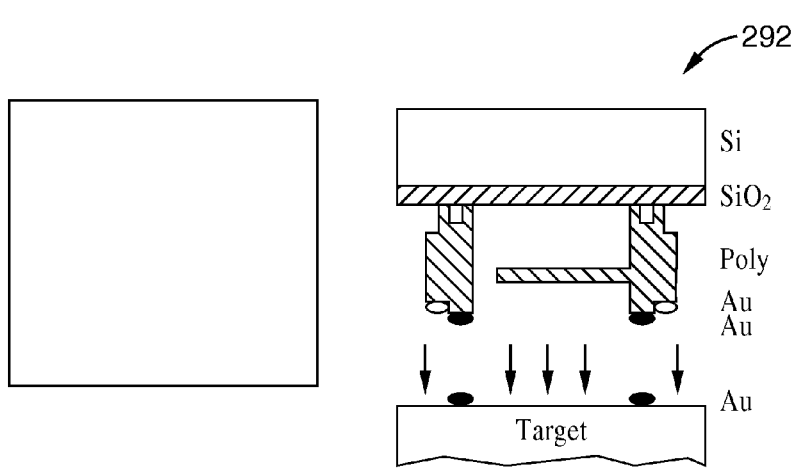
Figure 12V:
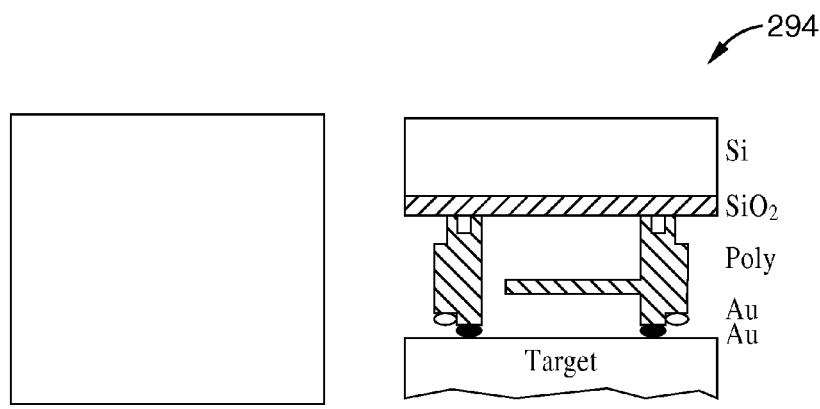
Figure 12W:
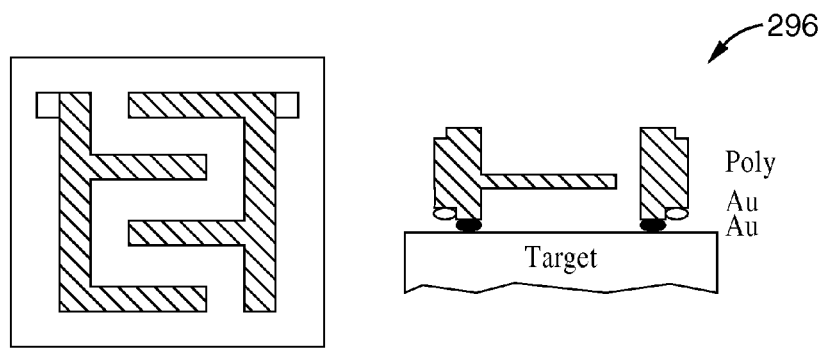

FIG. 12A through FIG. 12WW is a flow diagram showing an embodiment of a process for fabricating an inter-digitated capacitor strain sensor according to the present invention.

Figure 13:
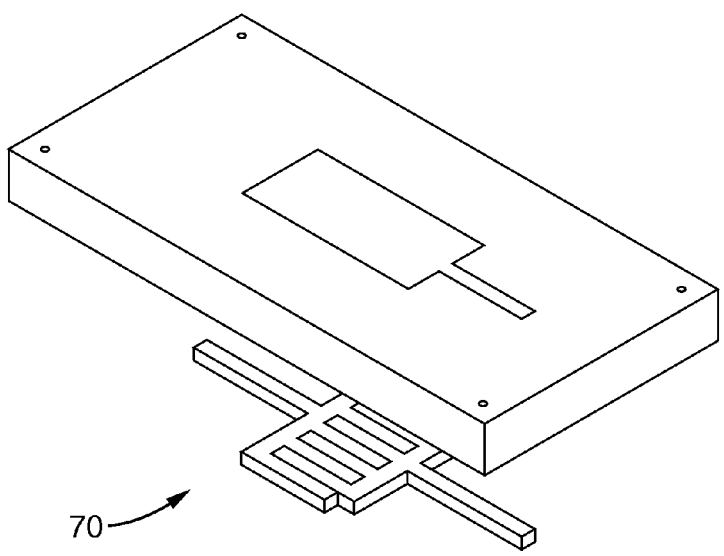
Figure 14A:
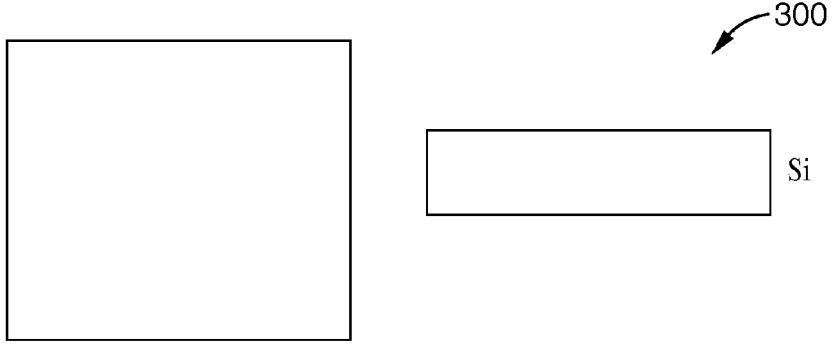
Figure 14B:
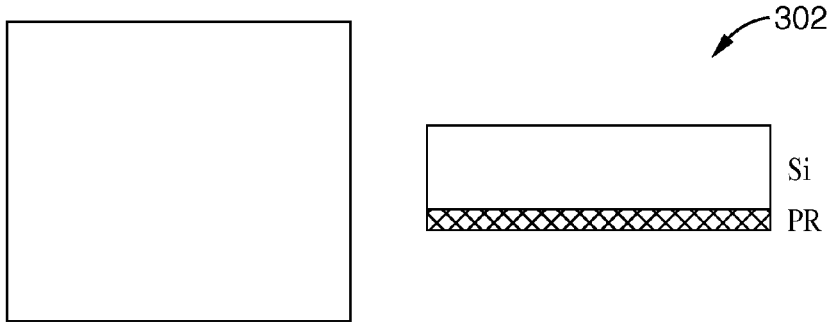
Figure 14C:
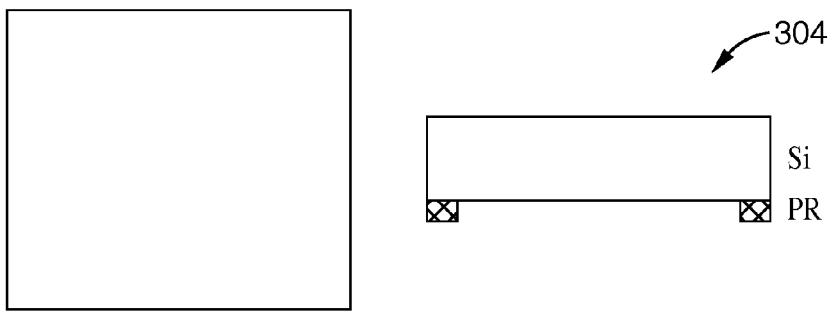
Figure 14D:
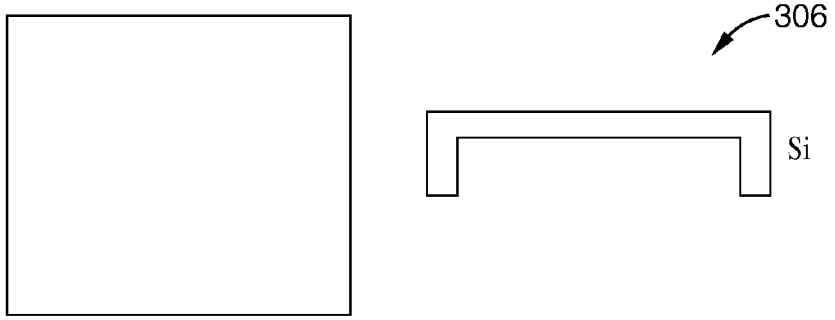
Figure 14E:
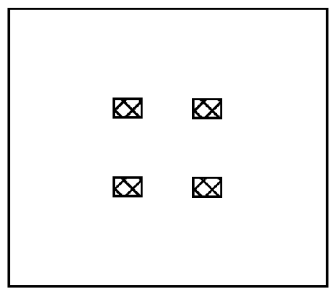
Figure 14E:
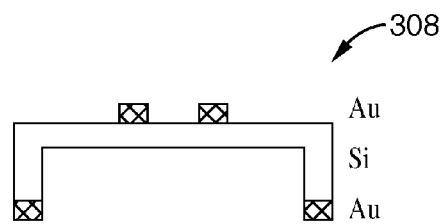
Figure 14F:
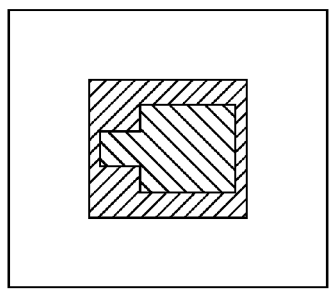
Figure 14F:
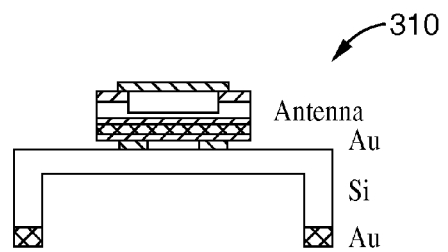
Figure 14G:
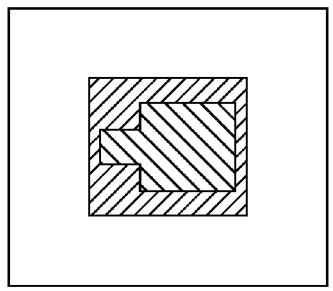
Figure 14G:
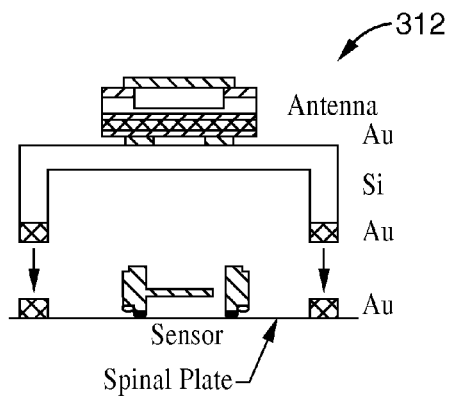
Figure 14H:
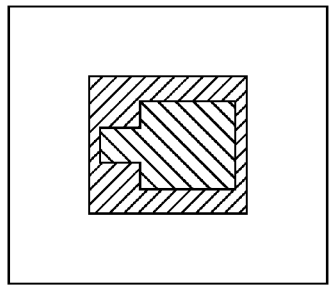
Figure 14H:
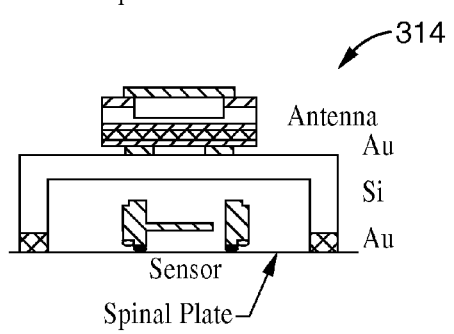

FIG. 13 is a perspective view of a packaging and mounting configuration for the inter-digitated capacitor of the present invention.

FIG. 14A through FIG. 14H is a flow diagram showing an embodiment of a packaging process for the inter-digitated capacitor and microstrip antenna according to the present invention.

Figure 15:
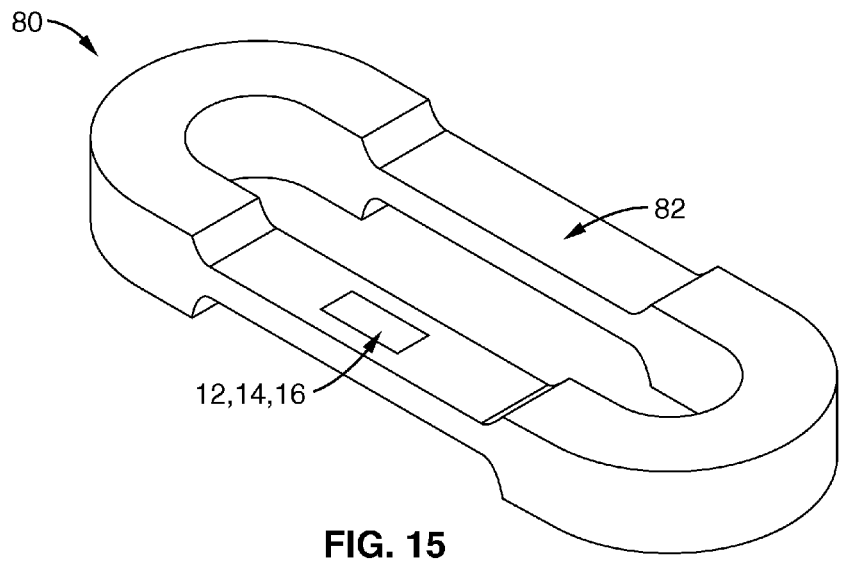

FIG. 15 is a perspective view of an embodiment of a spinal plate with an attached inter-digitated strain sensor according to the present invention.

Figure 16:
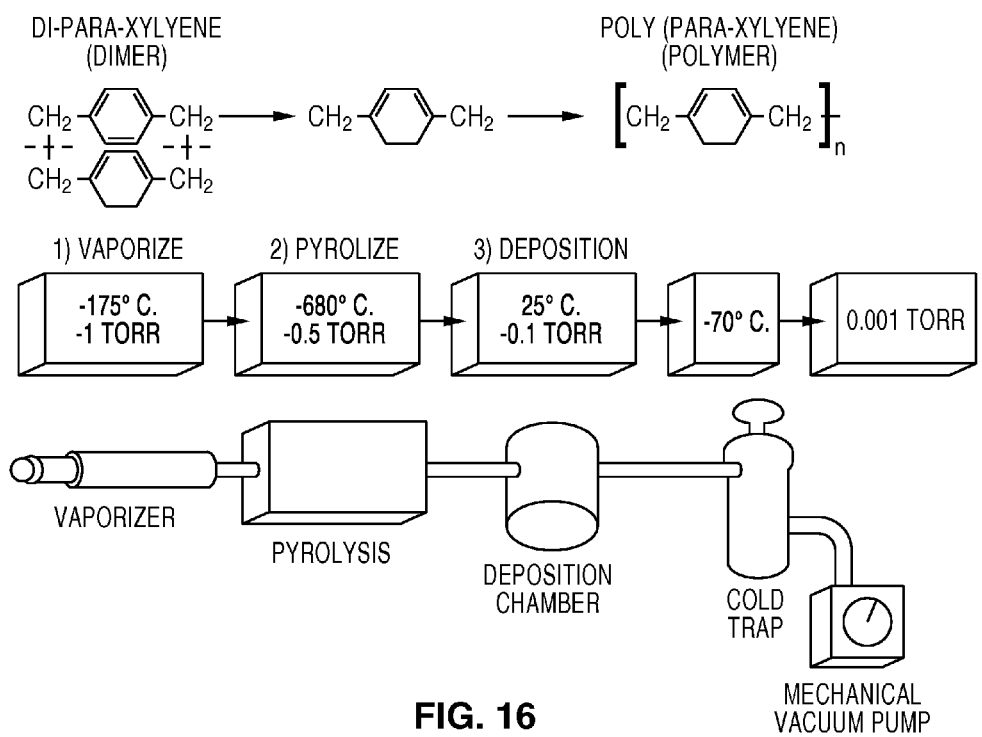

FIG. 16 is a flow diagram showing an embodiment of a process for applying a parylene sealant to a packaged antenna, inter-digitated capacitor strain sensor, and associated circuitry according to the present invention.

Figure 17:
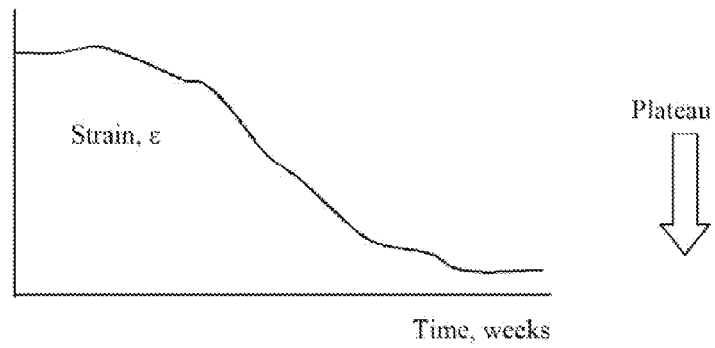

FIG. 17 is a graph illustrating expected strain decrease and plateau resulting from progression of spinal fusion.

Figure 18:
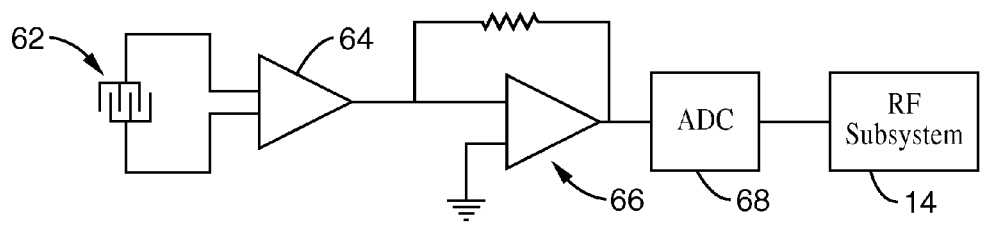

FIG. 18 is a schematic diagram of a digital telemetry and calibration circuit for use with an inter-digitated capacitor strain sensor system according to the present invention.

Figure 19:
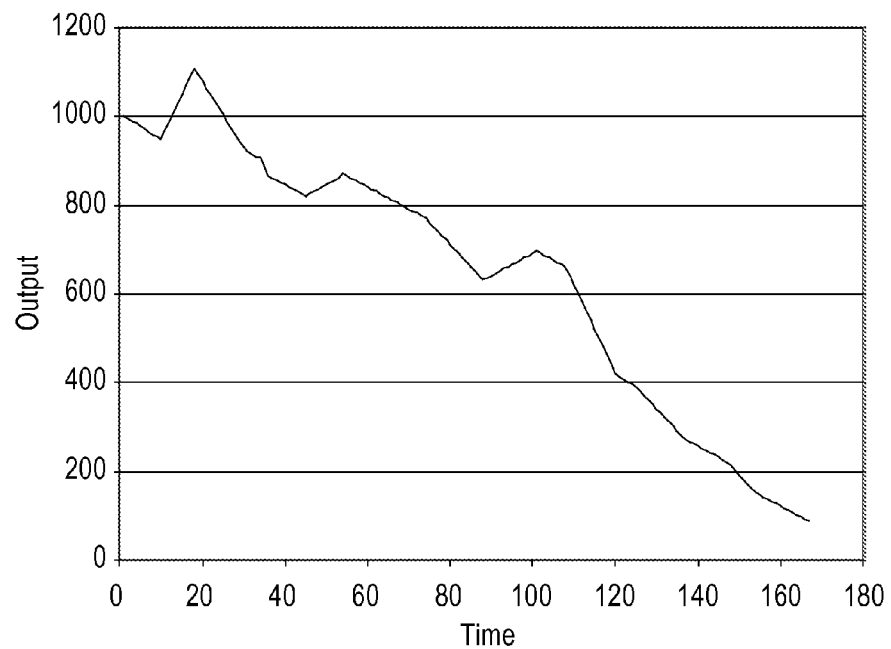

FIG. 19 is a graph illustrating an example of expected strain data output of an inter-digitated capacitor strain sensor system according to the present invention as a function to time during spinal fusion.

Figure 20:
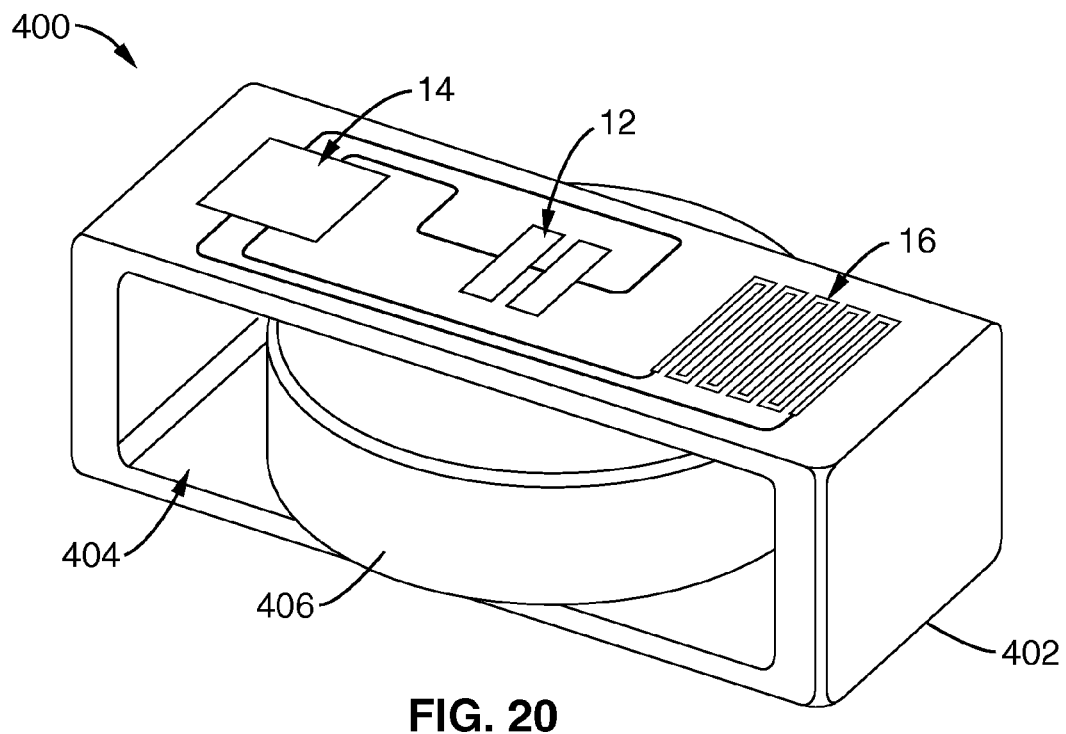

FIG. 20 is a perspective view of an embodiment of a blood chemical monitor employing an inter-digitated capacitor strain sensor according to the present invention.

Figure 21:
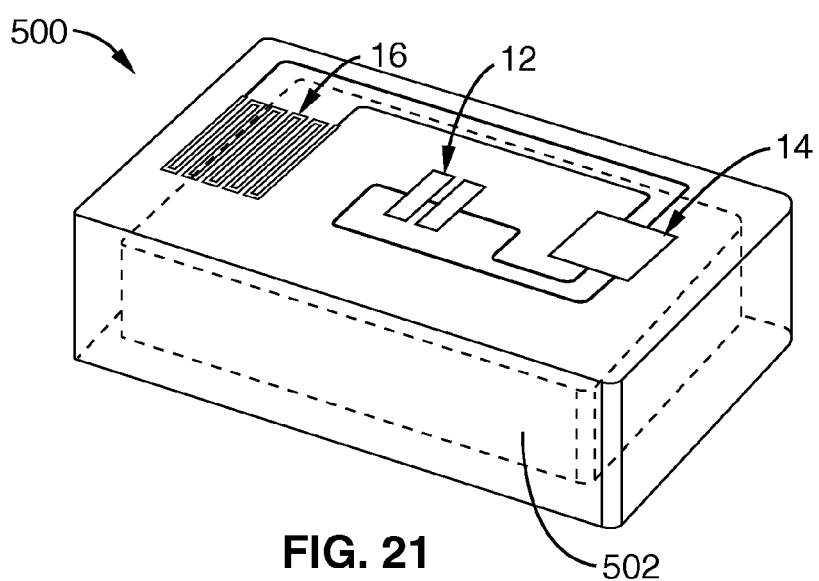

FIG. 21 is a perspective view of an embodiment of a sealed-chamber heart rate monitor employing an inter-digitated capacitor strain sensor according to the present invention.

Figure 22:
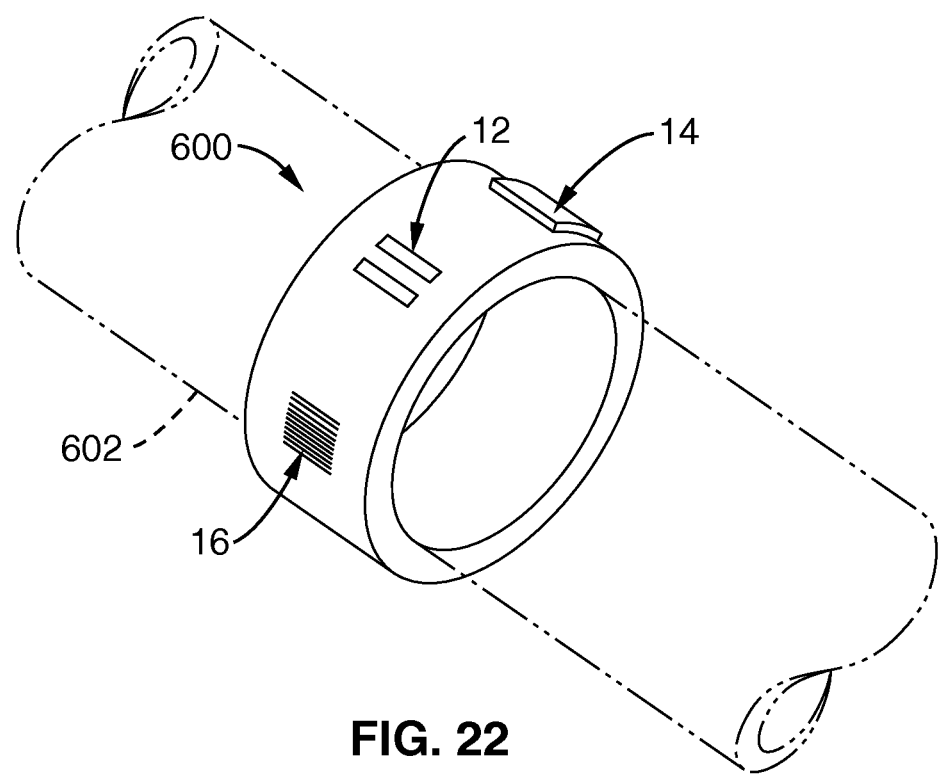

FIG. 22 is a perspective view of a heart rate monitor blood vessel cuff employing an inter-digitated capacitor strain sensor according to the present invention.

DETAILED DESCRIPTION OF THE INVENTION

Referring more specifically to the drawings, for illustrative purposes the present invention is embodied in the system, apparatus, devices and methods generally shown in FIG. 1 through FIG. 22.

In general terms, the present invention is embodied in a system that employs capacitive inter-digitated strain sensing and RF signal transmission using integrated microfabricated circuitry. The present invention generally comprises an implantable capacitive strain sensor that can produce a reliable, reproducible signal that will indicate via a radio telemetry signal when strain has changed. An embodiment of the system includes an internal power supply subsystem that is configured for inductive coupling to an external power source so that batteries are not required. A further embodiment of the system includes a receiver subsystem to which sensed data is transmitted and collected. Additional embodiments include variations of the foregoing.

The present invention will be described herein with reference to detecting spinal fusion. It will be appreciated, however, that practice of the invention is not limited to detecting spinal fusion. For example, the invention can be applied to measuring or monitoring strain in virtually any object, but is ideally suited to strain detection inside the body of a human or animal. According to other aspects of the invention, strain monitoring is used as an indicator of medical conditions including monitoring the progress of spinal fusion, monitoring glucose levels, measuring spinal loading, and monitoring heart rate, which will also be described herein. Therefore, the following description of the invention should be considered as non-limiting and provided by way of examples.

In one mode of operation, the present invention provides an electronic solution for detecting spinal fusion more rapidly than through the use of radiographs, and is based on the premise that the spinal fixation instrumentation used will not be rigid when initially implanted. For example, there will be minor gaps between the pedicle screws and the spinal plate that will allow for some movement. The screws will also move slightly until bone grows into the threads to hold them rigidly fixed. The anterior sides of the vertebrae are not fixed, and because the two vertebrae are separated by the cushioning intervertebral disc, there will always be some movement from this source. Therefore, the spinal plate anchored to the two pedicle screws will act like a beam with a moment applied at both ends. The moment will induce bending in the spinal plate that can be measured as a strain, especially if the spinal plate is necked down to provide a concentrated bending moment at the center of the plate. Initially, the strain on the spinal place will be large, but will decrease over time as the bone growth provides additional fixation. After some period of time, the strain will minimize at a lower value and remain relatively constant. By periodically sampling the strain electronically, a curve can be generated, showing the onset of rigid fixation.

To address the need to detect spinal fusion more rapidly, the invention comprises an electronic solution for detecting spinal fusion. The strain sensor and associated circuitry can be bonded directly to the spinal fixation device, which will share load with the bone. Thus, as the spine heals, the implant strain will diminish. There is a time dependent relationship between strain and fusion that can be detected by measuring strain in the spinal instrumentation. If spinal fusion can be detected by a radio telemetry system much earlier than a traditional radiograph, then time spent in bracing or modified activities for spine surgery patients can be minimized. Accordingly, an aspect of the invention is to reduce the amount of time patients must remain in a brace in order to avoid other complications, such as disuse atrophy, and that the patients' recovery and eventual outcome is thus improved.

In order to facilitate implantation of the implantable portions of the system, the circuitry can be integrated into the fixation plate or encapsulated and attached to the fixation plate. In this way, spinal fixation hardware will contain a strain sensor. Preferably, the implantable portion of the system is inductively powered by radio frequency to avoid the complications of implanting batteries within humans. Otherwise, batteries will be mounted subcutaneously and removed once fusion has been determined.

System Overview

Figure 1:
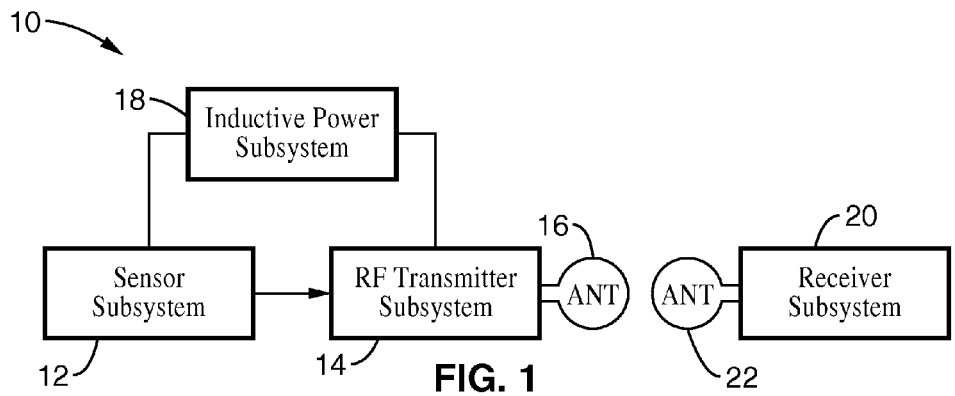
FIG. 1 is a functional block diagram of an embodiment of a strain sensing system according to the invention.

Referring first to FIG. 1, a strain measurement/monitoring system 10 according to the present invention is schematically illustrated. In the embodiment shown, the system comprises a sensor subsystem 12, a radiofrequency (RF) transmitter subsystem 14 and associated antenna 16, an inductive power subsystem 18, and a receiver subsystem 20 and associated antenna 22.

The technology for the receiver subsystem 20 and associated antenna 22 is commercially available, such as that used for RF ID applications. Such equipment will receive telemetry date as well as provide an inductively coupled power supply. It may, however, be necessary to modify the operating frequency of the equipment to match the desired operation frequency of the sensor system. Therefore, the following description will focus primarily on sensor subsystem 12, RF transmitter subsystem 14 and antenna 16, and inductive power subsystem 18.

RF Transmitter Subsystem

Figure 2:
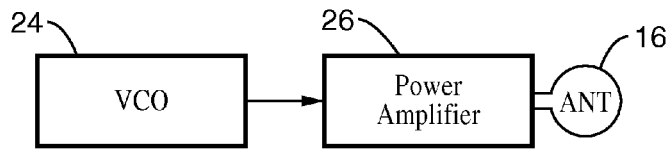
FIG. 2 is a functional block diagram of an embodiment of the RF transmitter subsystem in the system shown in FIG. 1.

In a preferred embodiment, the RF transmitter subsystem 14 comprises components that will receive the signal from the sensing subsystem 12 and use that signal to modulate the frequency (FM) of the carrier signal in order to transmit an output signal through the antenna 16. Referring also to FIG. 2, in the embodiment shown, the RF transmitter subsystem comprises a voltage controlled oscillator (VCO) 24 and a power amplifier 26 coupled to antenna 16. The power to drive this subsystem is supplied by an inductive power subsystem 18.

Frequency Selection

A factor in the overall design of the RF transmitter subsystem is the frequency at which the carrier signal will be transmitted. The operating frequency directly affects the dimensions of components in the RF transmitter subsystem, such as antenna 16. For the purpose of a design for use as a system implanted in the body of a human or animal, we chose a frequency of 100 GHz although other frequencies could be used. Higher frequencies tend to have better propagation characteristics and larger available bandwidth than lower frequencies, and allow for the use of a small antenna. Note, however, that safety limits of using such high frequency in a human body tends to restrict the electric field strength to approximately 61.4 V/m, the magnetic field strength to approximately 0.163 Nm, the power density to approximately 50 W/m$^2$, and the duration of exposure to less than approximately 6 minutes.

Modulation Type

Other potential safety concerns are related to the type of RF signal modulation scheme employed. There are generally three types of signal modulation; frequency modulation (FM), amplitude modulation (AM), and pulse modulation (PM). PM tends to cause the greatest damage to biological tissues due to high energy release during short time periods. On the other hand, AM is more susceptible to noise while being transmitted through biological tissue, thus leading to potential false data readings. Therefore, the amplitude is affected more than frequency. Consequently, frequency modulation (FM) is preferred because its amplitude is not relevant to the data transmitted and is safer than PM. An additional advantage of FM is the ability to have greater noise immunity at greater bandwidths. In summary, a frequency modulated signal transmitted in a wideband scheme is preferred.

Transmitter

Transmitter selection is also based on several factors. For example, the transmitter should be suitable for the modulating format selected as well as suitable for producing the required transmit power to provide a reliable link with the receiver subsystem. In the embodiment illustrated in FIG. 1 and FIG. 2, the transmitter comprises a voltage controlled oscillator 24 followed by a power amplifier 26. The modulator in this configuration is VCO 24 being driven by a modulating signal from the sensor subsystem 12.

Voltage Controlled Oscillator

It will be appreciated that the voltage controlled oscillator is an important component of the RF transmitter subsystem. VCOs in the GHZ range are typically fabricated using standard IC technology and are currently integratable. The objective of the VCO is to use an AC signal from the sensor subsystem 12 to modulate the signal of the VCO or the carrier signal. With zero input to the VCO, the VCO will produce a pure sinusoidal wave form with a fixed amplitude and frequency. When the VCO receives an input, it locks itself in a phase locked loop (PLL) to produce a signal that is modulated in relation to the modulating sensor signal.

The VCO preferably has a high tuning sensitivity (change in output frequency per unit change in the control voltage, Hz/V) that allows for maximizing the modulation of the carrier for an improved signal. In addition, power supply pulling (sensitivity of the output frequency to changes in the power supply voltage, Hz/V) should remain unchanged for improved gain. This type of behavior is expected during the power up of the circuit due to the transit behavior during this time. Therefore, initial readings may not be as accurate, and for this reason sufficient time should be allowed for each reading. Since the sensor is expected to produce very little change over the period of measurement, a consistent output from the system is a good indication of bypassing the transit time.

There are generally three types of voltage controlled oscillators that can be fabricated in integrated circuit form: ring, relaxation, and tuned oscillators. The first two are easier to implement in the present invention because they are monolithic and of small size when compared with tuned oscillators.

Figure 3:
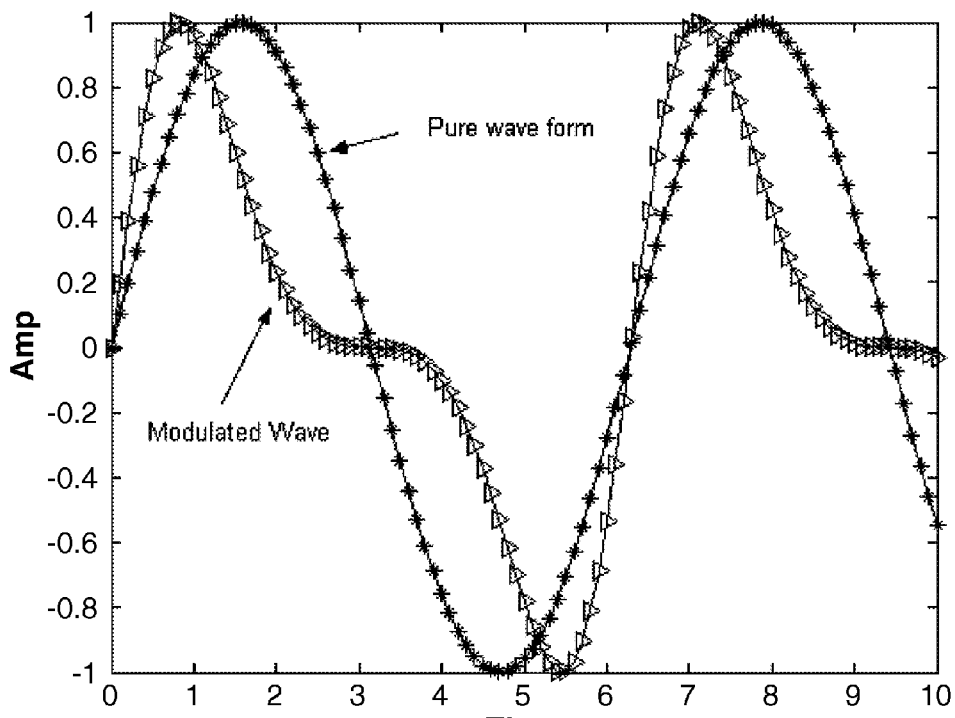
FIG. 3 is a graph illustrating waveform response of the voltage controlled oscillator shown in FIG. 2 to an AC modulated signal.

In the present invention, a ring oscillator is preferred. It will be appreciated that the general expression for carrier frequency is:

$$e(t)=A*\text{Sin}(\omega c*t+D*\text{Sin}(\omega m*t)) \quad (1)$$

where, $$D = \frac{2*\pi*f}{\omega m}$$

is deviation ratio or the modulating index, ωm=maximum sensor frequency, ωc=center frequency of the carrier, and A=Amplitude of the signal. The above equation indicates that a change in the amplitude of ωm changes the frequency of the carrier. FIG. 3 illustrates the expected response of a VCO when an input signal is provided. Note that the amplitude of the signal is constant while the frequency of the modulated signal is different than the pure sinusoidal wave of the VCO with zero input. This type of oscillator response is desired to affectively transmit the information with the least amount of noise from the medium.

Antenna

It will be appreciated that the antenna is an important component in any wireless communication system since it is the interface between the electronics inside the system and the outside world. It is well known that, as frequency increases, antenna size generally decreases. Microstrip technology provides a class of antennas that can be integrated onto the present invention quite easily, and is preferred due to due to the acceptable performance and the simple manufacturing process that is involved. Also, the shape of a microstrip antenna can be varied based on the needed radiation pattern. Square antennas produce good radiation characteristics and are widely used. An additional advantage of such antennas is their conformal configuration which can be placed on any metallic surface, planer or non-planar, which includes a spinal plate.

Figure 4:
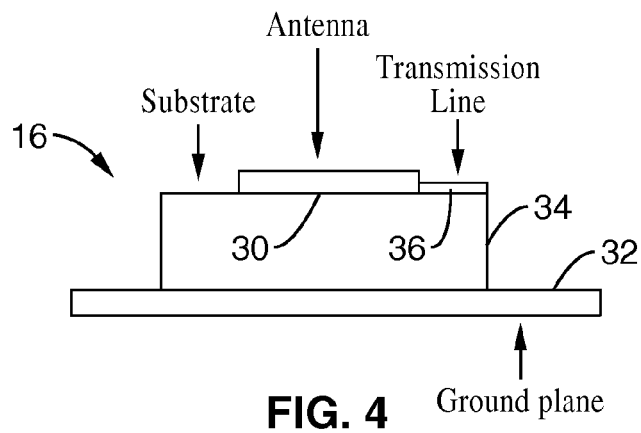
FIG. 4 is a cross-sectional schematic view of an embodiment of a microstrip antenna according to the invention.
Figure 5:
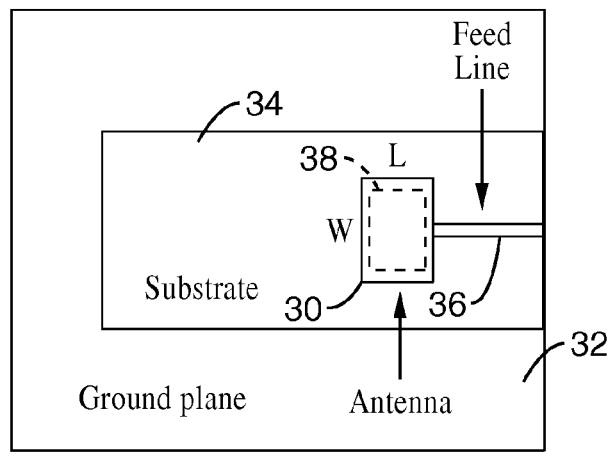
FIG. 5 is a top plan schematic view of an alternative embodiment of the microstrip antenna shown in FIG. 4.
Figure 6:
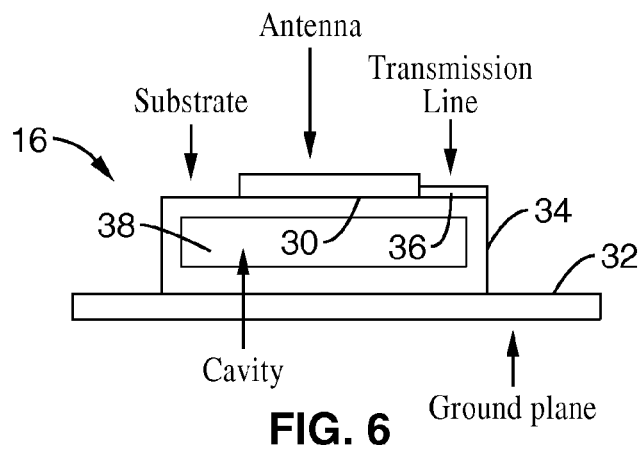
FIG. 6 is a cross-sectional schematic view of the microstrip antenna shown in FIG. 5.
Figure 7A:
FIG. 7A through FIG. 7R is a flow diagram showing an embodiment of a process for fabricating the microstrip antenna shown in FIG. 5 and FIG. 6.
Figure 7B:
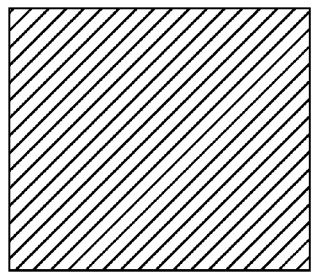
Figure 7C:
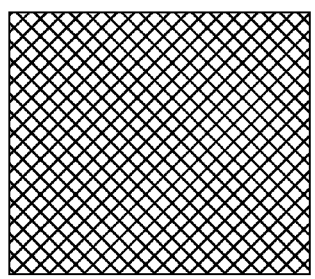
Figure 7D:
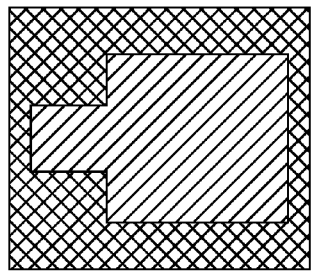
Figure 7E:
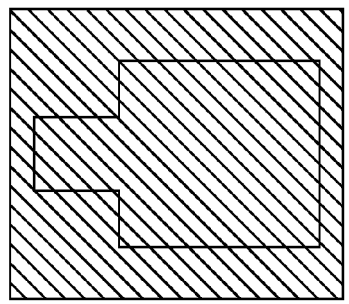
Figure 7E:
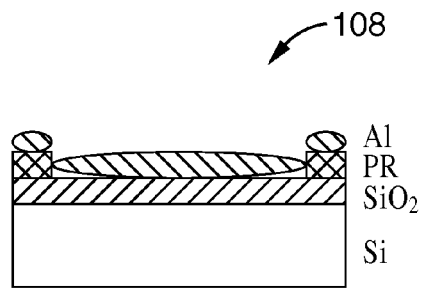
Figure 7F:
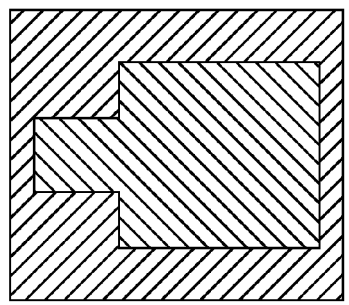
Figure 7G:
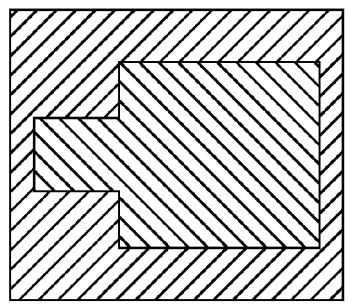
Figure 7G:
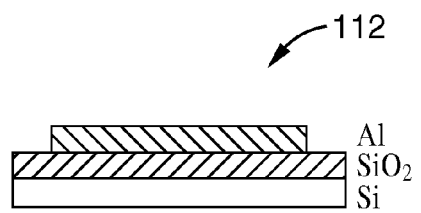
Figure 7H:
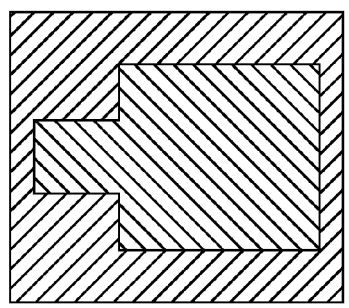
Figure 7I:
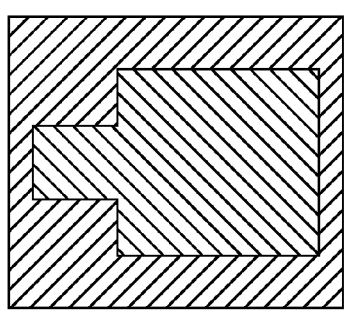
Figure 7I:
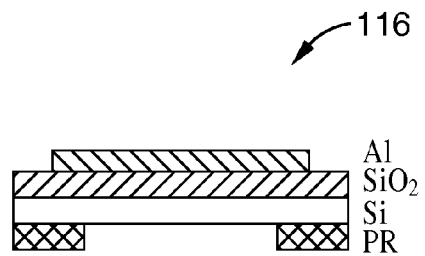
Figure 7J:
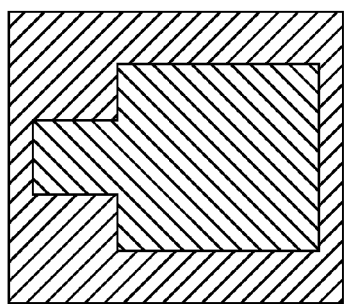
Figure 7J:
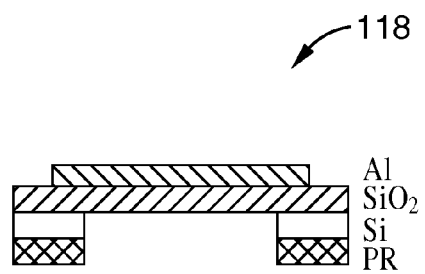
Figure 7K:
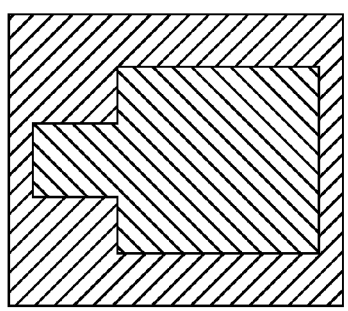
Figure 7K:
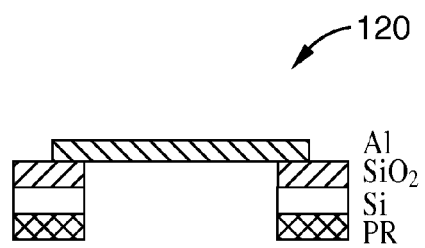
Figure 7L:
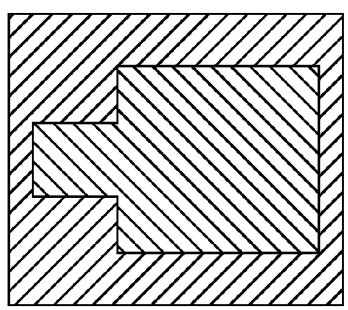
Figure 7L:
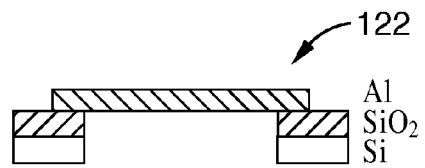
Figure 7Q:
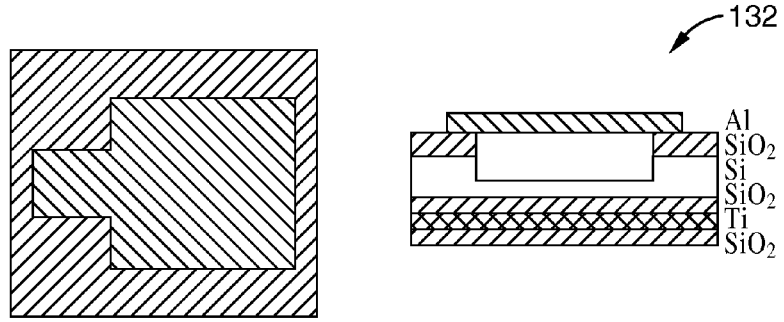
Figure 7R:
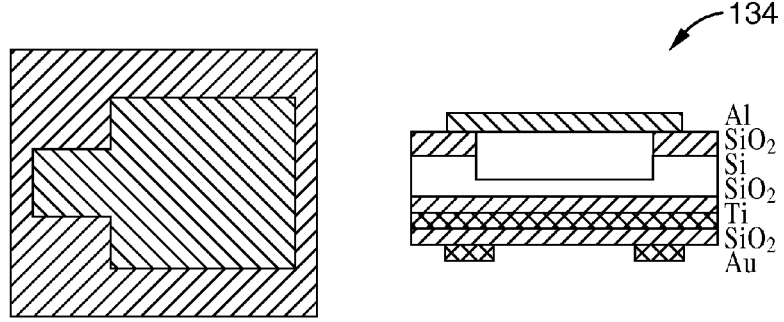

Referring to FIG. 4 through FIG. 6, the microstrip antenna 16 employed in the present invention comprises a very thin metallic strip (patch) 30 above a conducting ground plane 32, separated by a low-loss dielectric substrate 34.

A feed line 36 is also connected to the antenna. In this regard, there are several feed mechanisms that are available. The location of the feedline with respect to the antenna patch is determined by the radiation characteristics of the antenna. The simplest and preferred feed type is the microstrip feedline, an embodiment of which is illustrated in FIG. 4 through FIG. 6. In this embodiment, the feedline is in the same plane as the antenna and provides for a high degree of compactness and efficiency. Feedlines are important because they transfer the signal to the antenna. The impedance, ratio of voltage to current, of the feedline is the characteristic value and this determines the power loss during the transfer. It will also be appreciated that it is important to select a feed mechanism with minimal power loss.

As mentioned above, the preferred embodiment of the RF subsystem operates at a frequency of 100 GHz. This frequency is inversely related to the dimensions of the antenna as described by the following set of equations:

$$\text{Height of substrate } 0.003\lambda < h < 0.05\lambda \quad (2)$$

$$\text{Width of antenna patch } W = \frac{C}{2f_0}\left(\frac{\varepsilon r+1}{2}\right)^{-1/2} \quad (3)$$

$$\text{Length of antenna patch } L = \frac{C}{2f_0\sqrt{\varepsilon e}} - 2\Delta L \quad (4)$$

$$\varepsilon e = \frac{\varepsilon r+1}{2} + \frac{\varepsilon r-1}{2}\left(\frac{1+12h}{W}\right)^{-1/2} \quad (5)$$

$$\Delta L = 0.412h\frac{(\varepsilon e+0.3)*\left(\frac{W}{h}+0.264\right)}{(\varepsilon e-0.258)\left(\frac{W}{h}+0.8\right)} \quad (6)$$

where C=speed of light; ∈r=dielectric of substrate; ∈e=equivalent dielectric, and ΔL=change in length due to fringing fields at the ends.

Using the following Matlab algorithm to simulate the calculations, the dimensions for four antennas shown in Table 1 were calculated:

INDEX I:
Matlab script for the Microstrip antenna dimensions:
*************************************************
% program to calculate the dimensions for a rectangular microstrip
% antenna with a known thickness
% all dimensions in meters or SI units
% use assumptions from book: RF MEMS & the Humberto article on TTL
    microstrip antenna
*************************************************
c=3e8; % speed of light
f0= input(' frequency of operation= '); % frequency of operation
h= input('height of dielectric substrate= '); % thickness of the dielectric
    substrate
ebs__r= input(' Dielectric of material= '); % dielectric constant
w= c/(2*f0)*(((ebs__r+1)/2)^-.5) ; % width of the patch
ebs__e= (ebs__r+1)/2 + (ebs__r-1)/2 *(((1+12*h)/w)^-.5); % calculate
    effective K
    Num = (ebs__e+0.3)* ( w/h +0.264); % numerator of delta L,
    a dummy variable
    Den = (ebs__e - 0.258)*(w/h +0.8); % Denominator of delta L,
    a dummy variable
    deltaL= 0.412*h * (Num/Den) ;
l=(c/(2*f0)*(sqrt(ebs__e)))-2*deltaL );% length of the patch
w__mm =w*1000   % dimensions in mm
l__mm=l*1000    % dimensions in mm
h__mm=h*1000    % dimensions in mm
*************************************************

A preferred set of dimensions are those in row 3; namely, 0.15 mm×0.588 mm×0.463 mm. A dielectric material with a value of ∈=12 (such as silicon) is suitable for the substrate. The thickness of the antenna patch is not critical to the performance, and a thickness of 10 μm was chosen for this embodiment.

Note that in selecting a high dielectric constant, the substrate becomes electrically thick at higher frequencies; namely, λm/4 at 100 GHz, where λm is the wavelength inside the substrate. Higher thickness leads to increased surface waves and hence losses. Therefore, in the present invention, artificial methods are preferably used to reduce the effective dielectric constant of the substrate below the antenna. One method to do so is by micromachining the substrate and creating a cavity 38 under the antenna as shown in FIG. 5 and FIG. 6. The resulting substrate then comprises a composite of air and Si. This configuration can be achieved by, for example, a DRIE etching of the substrate under the antenna patch. Assuming a vertical wall etching, this method improves the antenna bandwidth and the efficiency over conventional substrates by as much as 60% and 28%, respectively. Preferably, the cavity is designed to have a resonant frequency close to that of the antenna patch to reduce losses.

When the cavity is added, the new effective dielectric constant is estimated to be:

$$\varepsilon r, \mathit{eff} = \frac{\varepsilon_{cavity}}{L + 2\Delta L}\left(L + 2\Delta L \frac{\varepsilon_{fringe}}{\varepsilon_{cavity}}\right) \quad (7)$$

where the dielectric constant for the fringing field region and the mixed substrate cavity region are given by:

$$\frac{\varepsilon_{fringe}}{\varepsilon_{cavity}} = \frac{\varepsilon_{air} + (\varepsilon_{sub} - \varepsilon_{air})x_{air}}{\varepsilon_{air} + (\varepsilon_{sub} - \varepsilon_{air})x_{fringe}} \quad (8)$$

$$\varepsilon_{cavity} = \frac{\varepsilon_{air}\varepsilon_{sub}}{\varepsilon_{air} + (\varepsilon_{sub} - \varepsilon_{air})x_{air}} \quad (9)$$

where $x_{air}$ and $x_{fringe}$ are ratios of air to substrate thickness in the mixed and fringing field regions. Note that with this cavity redesign, the dimensions of the antenna will change based on the new values of the dielectric constant of the mixed substrate region.

Analysis of the antenna radiation spectrum is then used to calculate the optimum location for receiving data from the system. The radiation pattern describes the angular variation of power density of the signal throughout space. The antenna radiation pattern is divided into two major regions; the far field and the near field. It is preferable to receive the waveform in the far field region to maximize the received signal and to ensure accurate readings.

Referring now to FIG. 7, in a preferred embodiment the microstrip antenna is fabricated in a similar manner to a parallel plate capacitor according to the steps shown. Top views appear on the left and cross-sectional views appear on the right.

The process begins at step 100 with a silicon wafer.

At step 102, the surface is passivated with thermal oxidation (2 μm).

At step 104, photoresist (PR) is spun onto the passivated surface.

At step 106, a first mask is used to pattern the antenna.

At step 108, aluminum is deposited using LPCVD.

At step 110, excess aluminum is lifted off using acetone.

At step 112, the silicon is etched from the backside using DRIE. The bottom side of the wafer is also polished down. This creates the dimensions of the air cavity.

At step 114, photoresist is spun onto the backside to create the air cavity.

At step 116, a second mask is used to pattern the air cavity. The PR is then exposed and developed.

At step 118, silicon is etched from the backside using RIE.

At step 120, SiO$_2$ is etched from the backside using BOE.

At step 122, the PR is removed using acetone.

At step 124, a second silicon wafer is fusion bonded to the etched wafer to create the air cavity.

At step 126, silicon is etched from the backside using DRIE and the bottom side of the wafer is polished down.

At step 128, SiO$_2$ is deposited on the backside to passivate the surface.

At step 130, titanium is sputtered on the backside to create the ground plane.

At step 132, SiO$_2$ is deposited on the backside for electrical isolation.

At step 134, gold bumps are patterned for "gold bump compression bonding."

Inductive Power Subsystem

It will also be appreciated that supplying power to a sensor for short- or long-term monitoring in human recipients can be a challenge. A generally unacceptable method of providing power would consist of having electrodes riveted to the patient's skin to connect the microsystem to the outside world for power and data collection. This "Frankenstein-like" solution could potentially work, but the risk of infection and injury to the patient makes this method of supplying power to the device less than appealing. Furthermore, due to the harsh environment inside the human body, the sensor cannot contain any toxic materials because in the event that the packaging was to fail, contamination of the biological host or damage to the microsensor system itself could occur. This constraint, along with a relatively short lifetime, eliminates the possibility of incorporating a chemical battery into the system.

Therefore, a more practical method is to supply power through a wireless medium. In the embodiment shown, magnetic coupling is employed for this purpose. The basic approach for supplying power magnetically is to induce a voltage onto a coil implanted into the biological host with the sensor. This is accomplished by exciting an external coil that is located directly over the implant, preferably using a conventional sinusoidal voltage supply (not shown) for excitation. The excitation signal passes through the body and into the internal coil where an alternating current (AC) voltage is induced. The induced voltage in the implanted coil is then rectified and filtered to create a direct current (DC) source for powering the sensor and associated RF transmitter circuitry. The method of magnetic coupling described above is a technology known as passive telemetry, or alternatively absorption telemetry.

Figure 8:
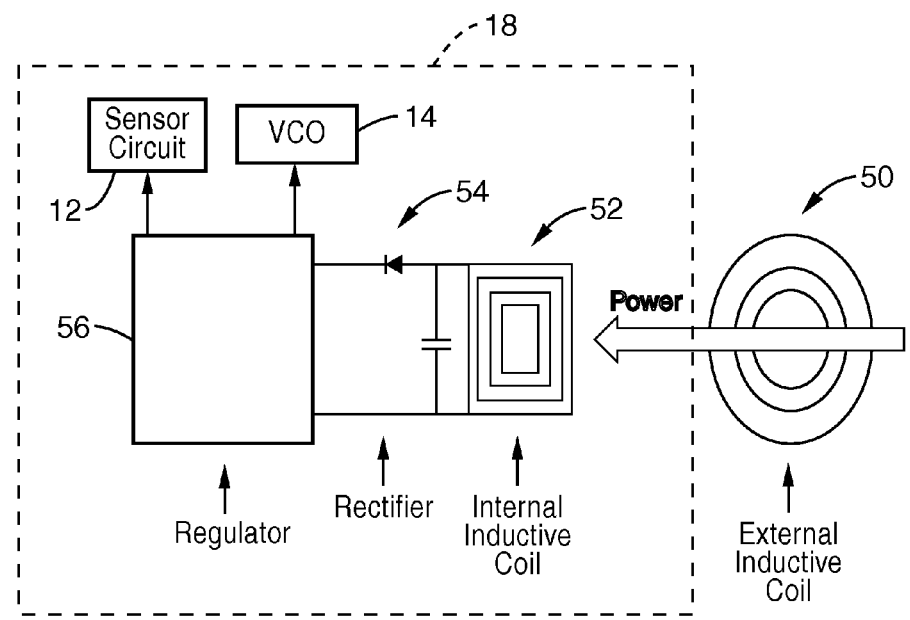
FIG. 8 is a schematic diagram of an embodiment of an inductive power supply subsystem according to the invention.

FIG. 8 illustrates various components of an inductive power subsystem 18 suitable for use in the present invention. This embodiment is shown in the context of receiving power from an outer inductive coil 50 which would be connected to the external sinusoidal power source, such as provided by an RF ID type receiver unit 20. In the embodiment shown in FIG. 8, the inductive power subsystem comprises an inner inductive coil 52, a rectifier 54, and a regulator 56. As can be seen, the internal inductive power unit essentially comprises a tuned LC receiver, formed by internal coil 52 and a capacitor 58, rectifier 54 and voltage regulator 56. It will be appreciated that the efficiency of power transmission is related to the degree of coupling of the outer coil 50 and the inner coil 52. Factors that affect this efficiency include shielding of the inner coil, the distance between the coils, and the orientation of the coils with respect to each other.

To improve the power link between the internal and external coils, the size of the two coils should be optimized for increased coupling coefficient. Other improvements may be made to the LC circuit of each coil if desired. To maintain a constant supply of DC voltage, a regulator followed by a rectifier are used as shown. Also, the internal coil can be macromachined instead of micromachined to increase efficiency. In addition, the inductive power subsystem is preferably hermetically sealed for protection and, to minimize the size of the internal power unit, the coil is placed outside the hermetically sealed unit and will be located on the implant itself. A wire connection then would be used between the inductive power subsystem and the sensor and the RF transmitter subsystem, and any other related circuitry.

Sensor Subsystem

Two sensing methods that were considered for measuring spinal fusion were (1) semiconductor-based resistive strain gages and (2) capacitive sensors. With resistive strain gages, minute changes in resistance are detectable. However, resistive strain gages have several drawbacks which make their use in sensing spinal fusion generally undesirable. First, looking at the power consumption of a resistive strain gage, there can be a fair amount of power dissipation due to the resistance (e.g., power dissipated=$I^2*R$). Second, resistive strain gages are temperature dependent devices and could provide unreliable measurements.

Therefore, in the embodiment shown, the sensor comprises a capacitive sensor. A capacitive sensor takes advantage of the absence of temperature dependence and the minimized power consumption. Because capacitive sensors are also generally known to be more sensitive than resistive sensors, a design based on a change in capacitance due to a change in strain should provide a more accurate measurement.

Two types of capacitive sensors that were considered for this purpose were (1) spacing variation motion sensors and (2) area variation motion sensors. In a spacing variation motion sensor, the change in capacitance is dependent on the spacing between the two conducting plates. However, a non-linear relationship exists between the spacing and capacitance change which presents a problem with measuring capacitance directly. On the other hand, in an area variation motion sensor, the change in capacitance is dependent on the area of overlap between the two conducting plates and capacitance and motion are linearly related. For purposes of sensing spinal fusion, an area variation motion sensor is preferred since capacitance and motion are linearly related and capacitance can be measured directly.

Note, however, that with a conventional area variation sensor, the capacitance change due to 25 μm of strain is on the scale of $10^{-16}$ F and therefore, is effectively too small of a change to measure accurately. Referring to FIG. 9, to solve this problem we designed an interdigitated capacitor 60 using fifty-one free-standing, inter-digitated fingers. This design yielded fifty parallel plate capacitors adding to the total capacitance measurement. As a result, we are able to sense a capacitance on the order of $10^{-14}$ F. Our capacitance sensing relies on the lateral movement of the inter-digitated fingers. The change in area between the fingers due to the lateral movement results in a change of capacitance. The basic equation for parallel-plate capacitance is $$C = [\epsilon_o \epsilon_r * A*(n-1)]/d = [(\epsilon_o \epsilon_r * W * l * (n-1)]/d \quad (10)$$

where $\epsilon_o = 8.85 \times 10^{-12}$ F/m is the permittivity of free space, $\epsilon_r = 1$ is the permittivity of air, "A" is the area of the plates, "d" is the gap between the plates, "W" is the width of the plates, "l" is the length of the plates, and "n" is the number of inter-digitated fingers.

Figure 9A:
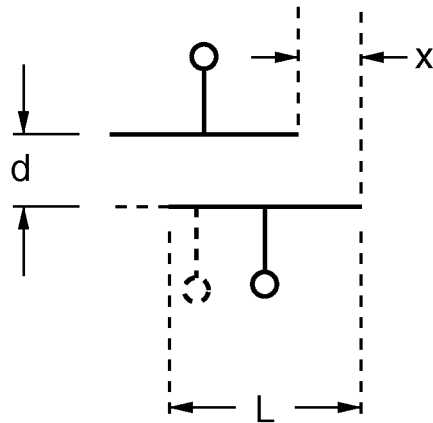
FIG. 9A is a schematic view of an area variation motion capacitor strain sensor employed in the present invention.
Figure 9B:
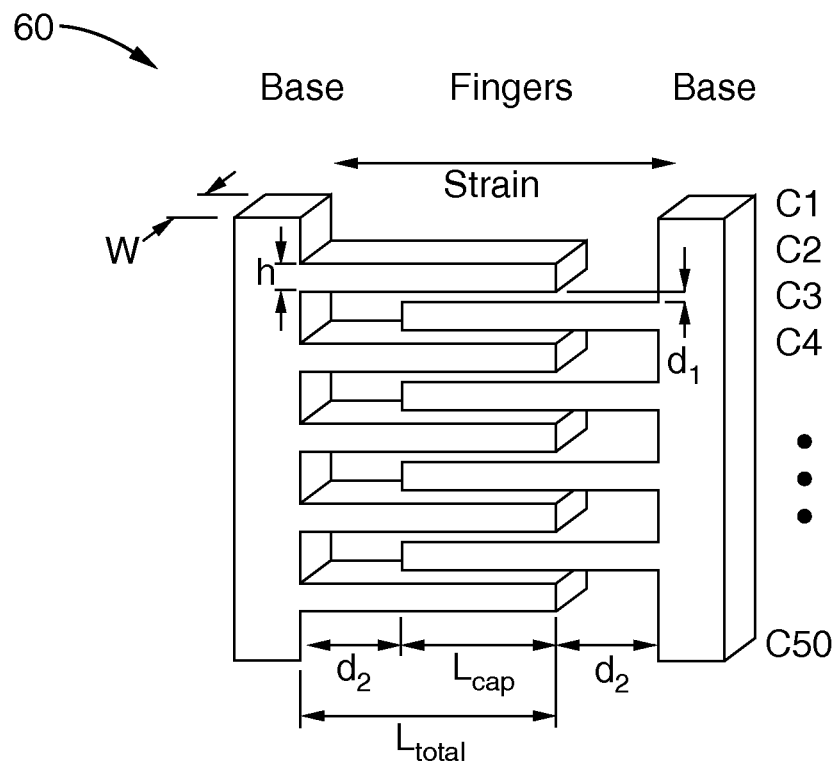
FIG. 9B is a perspective view of the structure of an inter-digitated area variation motion capacitor strain sensor according to the present invention.

Before spinal fusion occurs, there will be a strain induced from the bending of the vertebrae. By placing our capacitance sensor in the direction of this strain, a lateral movement of the plates will cause the area of the capacitor to change (FIG. 9A, FIG. 9B). The capacitance can then be calculated using $$C = [\epsilon_o \epsilon_r * w * (l-x) * (n-1)]/d \quad (11)$$

where "x" is the amount of displacement due to the strain (25 μm).

In addition to the capacitance created between each of the fingers, there is also a capacitance created between the tip of each finger and the opposing base. This capacitance changes as the gap between the finger and the base varies. Because we desire our overall capacitance to be a function of only the lateral variation capacitance between the fingers, we designed our sensor to minimize any capacitances that might result from tip of each finger and the opposite base. To minimize this capacitance, we designed the gap between the finger and the opposing base to be large enough that the overall capacitance is not affected by these space variation capacitances. As a result, we designed the gap, $d_2$, to be 50 μm.

We also chose our capacitor dimensions such that maximum displacement due to strain could be sensed. The inter-digitated fingers remain free standing and function properly as long as the length of each finger does not exceed approximately 200 μm. For this reason, we chose the total length of each finger, $L_{Total}$, to be 200 μm. Since we already declared the gaps, $d_2$, on each finger to be 50 μm long, the remaining 150 μm was assigned to the capacitance length, $L_{Cap}$ (FIG. 9B). By using the relationship between the capacitance, length, width, and gap, a large length and large width and a small gap are desired for a large capacitance value. Consequently, we chose a length "$L_{Cap}$" of 150 μm, width "$W_{Cap}$" of 20 μm, a gap "$d_1$" of 5 μm, and a height "h" of 20 μm. Using 51 inter-digitated fingers, our resulting capacitance under no strain is $$C_{NoStrain} = [(\epsilon_o \epsilon_r * w * l * (n-1)]/d = [(8.85 \times 10^{-12})*(1)*(5 \times 10^{-6})*(150 \times 10^{-6})*(50)]/10 \times 10^{-6} =$$
$$C_{NoStrain} = 3.34 \times 10^{-14} F \quad (12)$$

During a maximum strain of 25 μm, we found the capacitance to be $$C_{25\,\mu m} = [(\epsilon_o \epsilon_r * w * l * (n-1)]/d = [(8.85 \times 10^{-12})*(1)*(5 \times 10^{-6})*(150 \times 10^{-6} - 25 \times 10^{-6} * (50)]/(10 \times 10^{-6})$$
$$C_{25\,\mu m} = 2.60 \times 10^{-14} F \quad (13)$$

By carefully choosing these dimensions, we expect to maximize the capacitance measurement of our sensor.

Since capacitance and motion are linearly related for an area variation sensor, the capacitance can be measured directly. However, a transducer is still needed to translate the capacitance change response to an electrical output signal, in our case, we prefer a capacitance bridge to convert the capacitance changes into an electrical voltage output. Capacitance bridges are commonly used as transducers, which is primarily reason we chose to use it in our design.

Figure 10A:
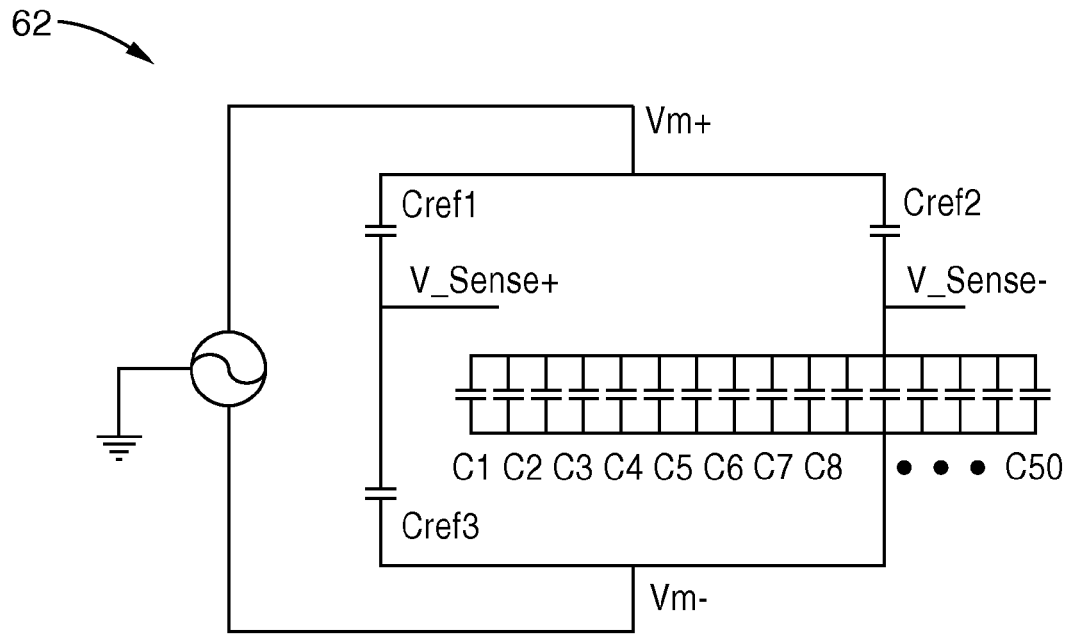
FIG. 10A is a schematic diagram of a capacitance bridge employing an inter-digitated capacitor strain sensor according to the invention.
Figure 10B:
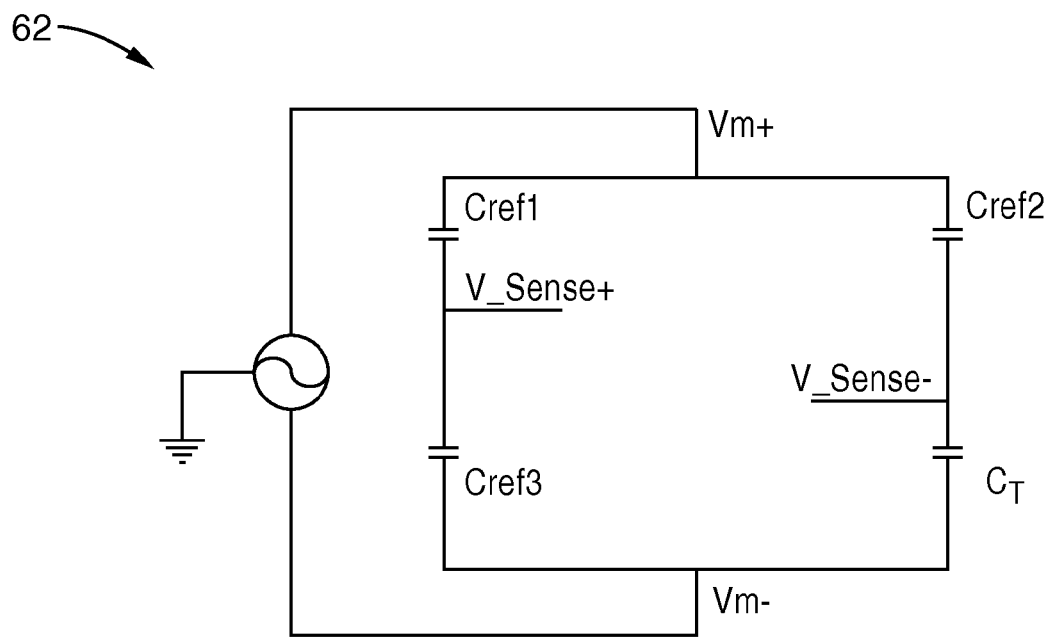
FIG. 10B is a schematic diagram of an equivalent circuit to the circuit shown in FIG. 10A.

Referring to FIG. 10, we designed our capacitance bridge 62 such that we combined the capacitances of all fifty capacitors as one of the four legs, $C_T$, of the capacitance bridge. The other three legs ($C_{ref1}$, $C_{ref2}$, and $C_{ref3}$) are set as reference capacitors. The reference capacitors are equal to $C_T$ during no strain:

$$C_{ref1} = C_{ref2} = C_{ref3} = C_{T\_No\,Strain} = 3.31 \times 10^{-14} F \quad (14)$$

When there spinal fusion has occurred, and therefore, no strain is present, we expect the voltage output at $V_{sense+}$ to equal the voltage output at $V_{sense-}$.

$$V_{sense+} = \frac{C_{ref1} * (2Vm)}{C_{ref1} + C_{ref3}} - Vm = \frac{C_{ref1} * (2Vm)}{C_{ref1} + C_{ref3}} - \frac{(C_{ref1} + C_{ref3}) * Vm}{C_{ref1} + C_{ref3}} \quad (15)$$
$$= \frac{(C_{ref1} - C_{ref3}) * Vm}{C_{ref1} + C_{ref3}}$$

$$V_{sense-} = \frac{C_{ref2} * (2Vm)}{C_{ref2} + C_T} - Vm = \frac{C_{ref2} * (2Vm)}{C_{ref2} + C_T} - \frac{(C_{ref2} + C_T) * Vm}{C_{ref2} + C_T} \quad (16)$$
$$= \frac{(C_{ref2} - C_T) * Vm}{C_{ref2} + C_T}$$

Figure 11:
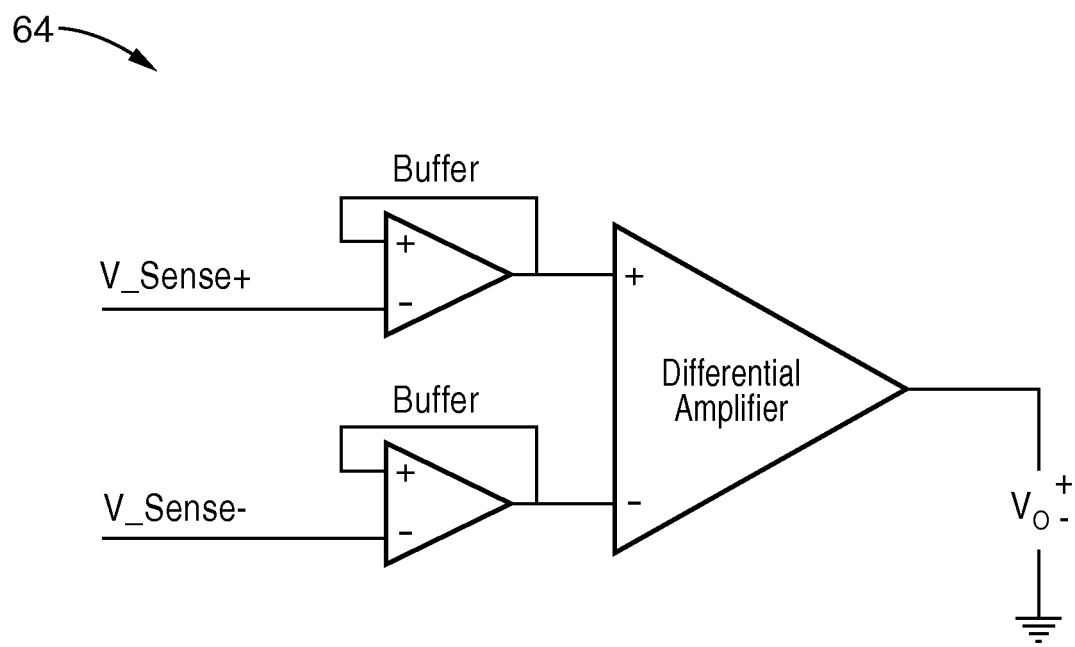
FIG. 11 is a schematic diagram of a differential amplifier employed in the inter-digitated capacitor strain sensor according to the present invention.

However, before spinal fusion has occurred, strain will be induced due to the bending of the vertebrate. During this time, we expect to see a difference between the output voltages, $V_{sense+}$ and $V_{sense-}$. In order to measure the voltage difference, a differential amplifier 64 with a single-ended output as shown in FIG. 11 can be used. A differential amplifier is a class of amplifiers that processes the difference between two signals. Our design includes unity gain buffers on each of the voltage outputs, $V_{sense+}$ and $V_{sense-}$, in order to isolate the nodes from other electronics. The signals are then each connected to the differential amplifier which in turn processes the difference between the two signals. Finally, the transducer output voltage, $V_o$, can be calculated using:

$$V_o = a_{cm} * \frac{V_{sense+} + V_{sense-}}{2} - a_{dm} * \frac{V_{sense+} - V_{sense-}}{2} \quad (17)$$

where $a_{cm}$ and $a_{dm}$ are the amplifying gains.

In a preferred embodiment, the fabrication of our sensor involves forty-nine steps and nine masks. The inter-digitated fingers are formed using polysilicon and released by wet etching sacrificial phososilicate glass (PSG). This process is shown in FIG. 12 where top plan views are shown on the left and cross-sectional views are shown on the right.

At step 200 the process begins with a silicon wafer.

At step 202, the surface of the wafer is passivated by thermal oxidation (2 µm).

At step 204, polysilicon (0.5 µm) is LPCVD deposited to create break-away tethers for the final release of the structure.

At step 206, photoresist (PR) is spun on the surface.

At step 208, a first mask is used to pattern the polysilicon break-way tethers. The PR is then exposed and developed.

At step 210, the polysilicon is etched using RIE.

At step 212, the PR is removed using acetone.

At step 214, a sacrificial PSG (1 µm) is deposited, and also provides some degree of planarization.

At step 216, PR is spun on the surface.

At step 218, a second mask is used to make anchor windows between the first and second layers of polysilicon. The PR is then exposed and developed.

At step 220, the PSG is partially etched in 10:1 HF to create connections to the break-away tethers.

At step 222, the PR is removed with acetone.

At step 224, a second layer of polysilicon (2 µm) is LPCVD deposited.

At step 226, PR is spun on the surface.

At step 228, a third mask is used to pattern anchors. The PR is then exposed and developed.

At step 230, the polysilicon is etched using RIE.

At step 232, the PR is removed using acetone.

At step 234, a second sacrificial PSG (3 µm) is deposited, and also provides some degree of planarization.

At step 236, PR is spun on the surface.

At step 238, a fourth mask is used to make anchor windows between the second and third polysilicon layers. The PR is then exposed and developed.

At step 240, the PSG is etched in 10:1 HF.

At step 242, the PR is removed using acetone.

At step 244, a third layer of polysilicon (20 µm) is LPCVD deposited.

At step 246, PR is spun on the surface.

At step 248, a fifth mask is used to pattern inter-digitated fingers. The PR is then exposed and developed.

At step 250, the polysilicon is etched using RIE.

At step 252, the PR is removed using acetone.

At step 254, a sacrificial PSG (22 µm) is deposited, and also provides some degree of planarization.

At step 256, PR is spun on the surface.

At step 258, a sixth mask is used to make anchor windows between the third and fourth polysilicon layers. The PR is then exposed and developed.

At step 260, the PSG is etched using 10:1 HF.

At step 262, the PR is removed using acetone.

At step 264, a fourth layer of politician (2 µm) is LPCVD deposited.

At step 266, PR is spun on the surface.

At step 268, a seventh mask is used to pattern anchors. The PR is then exposed and developed.

At step 270, the polysilicon is etched using RIE.

At step 272, the PR is removed using acetone.

At step 274, PR is spun on the surface.

At step 276, an eighth mask is used to make contact holes. The PR is then exposed and developed.

At step 278, gold is sputtered on the surfaces to create contacts (10 µm).

At step 280, the excess gold is lifted off using acetone.

At step 282, photoresist is spun on the surface.

At step 284, a ninth mask is used to pattern gold bumps for "gold bump compression bonding."

At step 286, gold is sputtered to create gold bumps.

At step 288, the excess gold is lifted off using acetone.

At step 290, the structure is released by etching the sacrificial PSG in 10:1 HF.

At step 292, the structure is flipped and aligned with a target spinal plate which also has gold bumps.

At step 294, the structure and target are compressed at room temperature.

At step 296, the bonded structure is released from the original substrate using the breakaway tethers.

In order to maximize the amount of strain sensed by the sensor, we want to minimize any adhesive, transitional material used between the sensor and the spinal plate. Such materials would attenuate the strain sensed by the sensor. As a solution, we utilized a technique called "gold bump compression bonding". This technique allows us to place our sensor directly on the spinal plate by patterning small, gold bumps on the sensor and the target spinal plate, aligning the two surfaces together, compressing them together at room temperature, and releasing the sensor from its substrate by severing its fragile, break-away tethers.

The circuitry for the RF devices and antenna serve as a housing to protect the inter-digitated fingers of the capacitive strain sensor from being contacted by sealant which is used to encapsulate the structure. Thus, the capacitive strain sensor is fabricated separately with gold tethers that hold the inter-digitated fingers in their correct position. Upon assembly, the capacitive strain sensor is inverted and pressed into mounting holes on the spinal plate. The tethers are then broken to release the inter-digitated fingers, thus allowing them to move with the bending of the spinal plate. Over this suspended, isolated capacitive sensor, the other circuitry and antenna are mounted with an open cavity on the underside to provide isolation for the capacitive sensor. Lead-through wires are used to attach the inductive power subsystem to the surface of the housing and additional lead through wires are used to attach the antenna and RF subsystem to the capacitive sensor. The housing is then sealed to the spinal plate using parylene. Parylene is preferred because it provides a conformal coating that will not be degraded by moisture.

FIG. 13 illustrates an embodiment of a packaging configuration 70. FIG. 14 illustrates a process for packaging the sensor and antenna in this manner where top plan views are on the left and cross-sectional views are on the right.

At step 300, the process begins with a silicon wafer.

At step 302, photoresist (PR) is spun on the backside of the wafer to create a cavity for the sensor.

At step 304, a mask is used to pattern the cavity.

At step 306, silicon is etched from the backside using DRIE, and the photoresist is removed.

At step 308, gold bumps are patterned for "gold bump compression bonding."

At step 310, the antenna is aligned and compressed to the top of the wafer.

At step 312, the structure is aligned with the spinal plate surface which also has gold bumps patterned on the surface.

At step 314, the structure is compressed onto the spinal plate at room temperature.

Note that the antenna is specifically designed to be small enough to fit within the form factor of the spinal plate and is on the same surface as the circuitry on the surface of the housing, and is the most external surface of the implanted device. It communicates via radio telemetry through the tissues and skin with a handheld RF reader. These readers are readily available through the well-established RFID tag market. To accommodate our 100 GHz frequency to limit the size of the antenna, a commercially available RF reader would require modification to sense higher frequencies. Alternatively, we would have to increase the size of our antenna which would require incorporating the antenna into the spinal instrumentation and use a wire coil rather than the surface micromachined patch antenna design described herein.

Spinal fixation plates and related hardware are well known in the art, and not described herein in any particular detail. However, there are certain features of the sensor system described herein that make modifications of a standard spinal plate worth consideration.

For example, it is desirable to fabricate the spinal plate, nuts, and pedicle screws from titanium. Titanium is nontoxic, hypoallergenic, biocompatible and exceptionally corrosion resistant. Titanium is also a nonmagnetic material. Since our sensors and circuitry will be mounted on the spinal plate, electromagnetic interference will be minimized by using titanium.

FIG. 15 illustrates a machined titanium spinal plate 80 with the sensor system described above attached. Note that, using the equations for bending in a beam, rigidly fixed at both ends and with an applied bending moment at both ends from the pedicle screws, we can obtain a strain of 25 µm with the sensor system. This is a very small signal, but well within the capabilities of our capacitive strain sensor. Although a portion of the beam shown in FIG. 15 has been machined down to create a concentrated bending location 82, the overall strength of the beam has not been compromised. The strength of the titanium plate has a generous safety factor, and actually only needs to remain intact until the bony ingrowth has finished. Long term, the strength of the fusion is provided entirely by new bone and not by the implanted hardware.

As indicated above, the system components can be sealed with a material such as parylene. This sealant can be applied, for example, using a process which is illustrated in flow chart form in FIG. 16.

The electronic strain measurement system described herein is designed to replace clinical x-rays, as they are often inconclusive until the bone has completely mineralized. During surgery, one of the spinal plates would be replaced with an electronically instrumented spinal plate. For humans, the goal would be to have all the instrumentation fitted onto an otherwise unaltered spinal plate.

In use for detecting the progress of spinal fusion, a handheld receiver unit would be brought into proximity of the sensor and an initial strain level would be recorded. Then, once a week during routine office visits, the handheld sensor would again be brought into proximity of the sensor to get additional strain level recordings. As shown in FIG. 17, over time, the level of strain should decrease and eventually plateau at a lower level. This should occur within eight to twelve weeks following surgery, at which time the fusion can be proclaimed solid and the patient's external bracing can be removed.

Referring now to FIG. 1, FIG. 10, FIG. 11 and FIG. 18, in one embodiment sensor subsystem 12 includes amplifier 64 as described above, as well as a second amplifier 66 and a 12-bit A/D converter 68. The output of the ND converter 68 provides a digital signal to RF subsystem 14. In this embodiment, the data can be transmitted as digital telemetry associated with the RF signal. Packet and other transmission techniques can be used as well.

In the digital telemetry embodiment illustrated above, prior to implantation, the inter-digitated capacitor strain sensor is preferably set to a "neutral" baseline. For example, this may be accomplished using the above-described operational amplifiers with a 12-bit A/D resolution that creates 4096 databits. The databits would be subdivided so that a percentage of the databits represents an equivalent range of the known values of strain for the area of interest. If, for example, a spinal implant experiences 1000µ∈ (microstrain) when implanted, each 1µ∈ would correspond to approximately 4 databits. Therefore, a neutral baseline value would be 2048 databits prior to implantation.

Amplifier 64 should never saturate; if it does, the output data becomes unusable. The system may still output a databit value, but it will be a constant value, virtually unvarying over the entire measurement period. The external receiver subsystem is preferably configured to detect this failure mode. This can be corrected by resetting the neutral baseline to a new value until it is within range.

The second amplifier 66 is employed to set the operating range of the device. For example, in spinal implants a normal range of strain is approximately 100µ∈. The second amplifier 66 is thus preset to represent +/−100µ∈ or a range of 200µ∈. In a 12-bit A/D, this corresponds to 1µ∈ change for every 20 databits of change in the strain.

Note also that, in some applications, the inter-digitated capacitor sensor and implant hardware are subjected to an initial strain by the surgeon. For example, in spine surgery, the torque applied to the pedicle screws induces approximately 600µ∈ in the spinal hardware. Thus, the inter-digitated capacitor sensor is preferably adjustable to re-center its value at the example 2048 databits. As the exact amount of induced strain cannot be predetermined, this adjustability is important for good performance of the sensor system.

Depending on the application, the strain after insertion or implantation will either increase, decrease, or oscillate with time and conditions. In a spinal fusion application, the spinal implant hardware may initially be in flexion or extension, depending on the completely variable orientation of the pedicle screws, plates, rods, or cages. For example, databit values below 2048 may indicate extension and values above 2048 may indicate flexion. Thus, the external receiver subsystem that communicates with the inter-digitated capacitor sensor should be able to analyze the initial change in strain from baseline and deduce the initial orientation of the spinal hardware. This information would then be stored in the external receiver subsystem for use in an algorithm that calculates the actual change in strain. Over time, the overall strain may decrease towards a plateau value, but the "sign" of this change is dependent on the initial orientation.

It will be appreciated that, although the system has been described above in the context of detecting spinal fusion, strain can be used as an indicator of other biomedical conditions as well. Using MEMS transduction, the system allows for the implantation or insertion of an inter-digitated capacitor strain sensor into area of interest. Advantageously, the system employs a sensitive inter-digitated capacitive strain sensor and RF transmitter subsystem are microscopic in size, temperature-independent, use no batteries, use biocompatible materials, are sealed from the environment, and can easily be integrated into an implant or used as part of a self-contained transponder unit. Preferably, RF frequencies are used which fall within publicly available bands and which are safe to biological tissues. In essence, the system can be considered a lifetime implant.

As described above, the RF transmitter subsystem communicates sensor information to an external receiver subsystem, which may, for example, comprise a commercial RF ID tag type receiver. The receiver subsystem may be embodied in many forms such as a handheld unit, portable unit, or wristwatch-style unit, and even contain data processing capabilities or capabilities to interface with a computer.

Preferably, algorithmic information used for data processing can be stored, processed, and analyzed externally thus keeping the system small in size and allowing for use of an inductive power subsystem. In an alternative embodiment, the system may include memory or the like for storing databit information from the sensor. This will provide the option of recording periodic or random time points for later analysis, and can provide for short-term or long-term storage. A healthcare professional, for example, would later query the device with a transmitter and signal it to download its stored data. The device could optionally be erased after download for long term studies. This configuration would require use of an external transceiver for bidirectional communication as an alternative to the receiver subsystem previously described. In addition, since data would be stored, this enhanced embodiment of the system would likely require a replaceable and/or rechargeable power source subcutaneous to the skin.

In addition, the external wireless transceiver can be configured to process the databit information received if desired. For example, the transceiver could include a processor and associated software that subtracts the databit information from the carrier RF wave, averages the databits into a single value, and applies the appropriate algorithms to convert the databit reading into a useable number. A 1000 Hz transceiver gathering strain information for one second would generate 1000 databits for each reading. If the averaged value were 2500 databits, the output strain would be $12.5\mu\varepsilon$. This would be added to the baseline value of perhaps $600\mu\varepsilon$ and give a reading to the surgeon of $612.5\mu\varepsilon$. Each of these averaged values could be recorded over time to show trends in the strain, such as a slow decline and eventual plateau in spinal strain such as illustrated in the example shown in FIG. 19. In some applications, user education may be needed if the user or patient can influence the sensor reading by, for instance, body position. If necessary, an operating protocol might be needed to inform the user how to orient the patient for consistent readings over a long term study.

As indicated above, the system is applicable to detecting biomedical conditions in general and has far reaching application. For example, referring to FIG. 20, a sensor apparatus 400 is shown that can be used for measurement of blood chemicals, factors, and minerals using MEMS. In this embodiment, the inter-digitated capacitor sensor would, for example, be inserted into the forearm with a syringe into forearm, or tethered inside a vein as needed to expose sensor to blood stream. The sensor would be mounted on a housing 402 that includes a chamber 404 containing a hydrogel, hydrophilic polymer, or other biocompatible material 406 that dynamically and reversibly swells when exposed to specific chemicals. High selectivity would be a crucial characteristic of the hydrogel. For example, glucose and lactate are both found in the blood, and have similar affinities in many hydrogels. It is important to thus test the marker of interest against potential competitive markers. FIG. 20 illustrates one configuration for a blood chemical sensor with a disc of polymer 406 swelling to induce a strain.

Swelling of the hydrogel, polymer or other material would induce a strain in the inter-digitated capacitor sensor that would be transmitted by its corresponding transponder. This strain would correspond to a specific concentration of specific marker within the blood and bodily fluids, such as glucose, electrolytes, sodium, hydration level, pH, toxic chemicals, or heavy metals (lead, mercury, chromium, etc). Thus, the strain can inform the user of a high or low level of a specific marker of interest. This would be of extreme interest to diabetics, endurance athletes, and military personnel in the field.

In this embodiment, an external wireless transceiver, most likely a wristwatch-style device, would analyze the strain information and process it with an algorithm to display glucose level, electrolyte levels (perhaps several key variables on one unit), etc. in terms commonly used for that application. Potentially, the wristwatch-style transceiver could communicate with a remote location for monitoring and advice by a professional, such as the user's physician or a military person's superior officers. The wristwatch style unit could also be configured to provide alerts or alarms to tell the user to take a specific action, such as replenish electrolyte levels, seek immediate medical attention, or inject insulin.

Similarly, the system could be configured for measurement of heart rate. Similar to the application described above with reference to FIG. 20, a heart rate monitor inter-digitated capacitor sensor could be simply injected by syringe beneath the skin, since the entire body "pulses" upon each beat of the heart. For an injected version, the sensor would have a sealed chamber that would flex under the pressure of each pulse and induce a strain that would be transmitted wirelessly to a wristwatch-style unit to give the user continuous heart rate monitoring. FIG. 21 illustrates an embodiment of a heart rate monitor 500 with a sealed chamber 502. Alternatively, as illustrated in FIG. 22, an inter-digitated capacitor sensor could be configured as a blood vessel cuff for attachment around a blood vessel 602 of the forearm (or other desirable region of the body) for larger strain potentials. If needed to achieve a strain above the background noise of the body, the sensor could be designed to cuff the external surface of blood vessel. This would induce a hoop stress and would maximize the strain potential from the blood vessel.

As described above, the preferred sensor configuration comprises an inter-digitated capacitor sensor. It will be appreciated that other types of sensors could be used, but that an inter-digitated capacitor sensor is clearly advantageous. Other types of sensors, although inferior to the inter-digitated capacitor sensor, include microfabricated pies-resistive strain gages configured in a Wheatstone bridge. In this configuration, change in resistance of the bridge is monitored as a voltage, converted to a digital signal, and transmitted to a handheld receiver.

Also as described above, in order to create a successful data acquisition system, several technologies must be integrated together that are driven by the microsensor design. The quantity to be measured and the environment that the sensor will reside in will determine the type of sensor, and the packaging needed to protect it from the potentially harsh surroundings. Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

Calculated Dimensions of Microstrip Antenna (m)

| Dimensions | f | L | h | W | $\epsilon$ |
|---|---|---|---|---|---|
| 1 | 100 GHz | 2.29 * 10E-4 | 1 * 10E-3 | 9.49 * 10E-4 | 4 |
| 2 | 100 GHz | 7.98 * 10E-4 | 1.5 * 10E-4 | 9.49 * 10E-4 | 4 |
| 3 | 100 GHz | 4.63 * 10E-4 | 1.5 * 10E-4 | 5.88 * 10E-4 | 12 |
| 4 | 100 GHz | .0056 | 1.5 * 10E-4 | .0059 | 12 |

What is claimed is:

1. A strain sensor apparatus, comprising:
a plurality of free-standing, inter-digitated fingers arranged to form an area variation inter-digitated capacitor to provide a capacitance;
wherein said inter-digitated fingers are coupled to a surface in a configuration to allow movement with bending of the surface;
wherein a change in area between the inter-digitated fingers due to lateral movement of the inter-digitated fingers results in a change of capacitance; and
wherein said strain sensor apparatus is adapted for implantation into a biological host for detecting strain.

2. An apparatus as recited in claim 1, further comprising:
a transmitter coupled to the inter-digitated capacitor; and
an antenna coupled to the transmitter;
wherein said inter-digitated capacitor functions as a sensor;
wherein said sensor, said transmitter, and said antenna are adapted for implantation in a biological host; and
wherein said sensor is encapsulated in a housing such that the sensor is sealed from the environment within the biological host.

3. An apparatus as recited in claim 2, wherein said transmitter and said antenna form said housing for encapsulating said sensor.

4. An apparatus as recited in claim 1, wherein lateral movement of the inter-digitated fingers and said change in capacitance are linearly related.

5. An apparatus as recited in claim 1, wherein said inter-digitated capacitor has a sensitivity of $10^{-14}$ F.

6. An apparatus as recited in claim 2, wherein said transmitter comprises a radio frequency transmitter.

7. An apparatus as recited in claim 2, wherein said transmitter comprises:
a voltage controlled oscillator; and
an RF power amplifier.

8. An apparatus as recited in claim 2, wherein said transmitter has an operating frequency of 100 GHz.

9. An apparatus as recited in claim 2, wherein said transmitter comprises a frequency modulation transmitter.

10. An apparatus as recited in claim 7, wherein said voltage controlled oscillator comprises a ring oscillator.

11. An apparatus as recited in claim 2, wherein said antenna comprises a microstrip antenna.

12. An apparatus as recited in claim 11, wherein said microstrip antenna comprises:
a conducting ground plane;
a low-loss dielectric substrate positioned on said ground plane; and
a thin metallic patch positioned on said dielectric substrate.

13. An apparatus as recited in claim 12:
wherein said substrate has a dielectric constant;
wherein said substrate includes a cavity; and
wherein said cavity reduces the dielectric constant of said substrate.

14. An apparatus as recited in claim 2, further comprising:
a power supply;
said power supply configured for inductive coupling to a power source;
said power supply coupled to said sensor and said transmitter;
wherein said power supply is adapted for implantation in a biological host.

15. An apparatus as recited in claim 14, wherein said power supply comprises:
an inductive coil;
a rectifier coupled to said inductive coil; and
a regulator coupled to said rectifier.

16. An apparatus as recited in claim 1, further comprising a calibration circuit for calibrating said sensor by adjusting a baseline characteristic of said sensor.

17. An apparatus as recited in claim 1, wherein said sensor is adapted for monitoring glucose levels.

18. An apparatus as recited in claim 1, wherein said sensor is adapted for monitoring heart rate.

19. An apparatus as recited in claim 1, wherein said sensor is configured for detecting a biomedical condition selected from the group consisting essentially of measurement of blood chemicals, factors, and minerals, glucose, electrolytes, sodium, hydration level, pH, toxic chemicals, or heavy metals.

* * * * *